(12) United States Patent
Kader et al.

(10) Patent No.: US 8,030,063 B2
(45) Date of Patent: Oct. 4, 2011

(54) SYSTEMS AND METHODS FOR VITRIFYING TISSUE

(75) Inventors: Amr Farouk Abdel Kader, Cleveland, OH (US); Tomasso Falcone, Shaker Heights, OH (US); Helmuth Kotschi, Middleburg Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 41 days.

(21) Appl. No.: 12/487,372

(22) Filed: Jun. 18, 2009

(65) Prior Publication Data

US 2010/0151570 A1 Jun. 17, 2010

Related U.S. Application Data

(60) Provisional application No. 61/073,392, filed on Jun. 18, 2008.

(51) Int. Cl.
*C12M 1/00* (2006.01)
*C12N 5/00* (2006.01)
*G01N 1/42* (2006.01)

(52) U.S. Cl. ........ 435/307.1; 435/1.1; 435/1.2; 435/1.3; 435/260; 435/374; 422/547; 73/864; 73/864.16; 73/864.91

(58) Field of Classification Search ............ 435/307.1, 435/374, 1.1, 1.2, 1.3, 260; 422/547; 73/864, 73/864.16, 864.91
See application file for complete search history.

(56) References Cited

U.S. PATENT DOCUMENTS

| | | | | |
|---|---|---|---|---|
| 4,184,483 | A | * | 1/1980 | Greenspan .................... 600/572 |
| 5,681,740 | A | * | 10/1997 | Messier et al. ............ 435/284.1 |
| 6,519,954 | B1 | | 2/2003 | Prien et al. |
| 6,533,933 | B1 | * | 3/2003 | Stankowski et al. .......... 210/232 |
| 6,615,592 | B2 | | 9/2003 | Prien et al. |
| 7,087,370 | B2 | | 8/2006 | Forest et al. |
| 7,157,222 | B2 | | 1/2007 | Khirabadi et al. |
| 7,278,278 | B2 | | 10/2007 | Wowk et al. |

(Continued)

FOREIGN PATENT DOCUMENTS

EP 0 364 633 A1 4/1990

(Continued)

OTHER PUBLICATIONS

Camus et al., "The Comparison of the Process of Five Different Vitrification Devices", *Gynecol. Obstet. Fertil.* Sep. 2006; 34(9):737-45 (Abstract only).

(Continued)

*Primary Examiner* — Nathan Bowers
*Assistant Examiner* — Gautam Prakash
(74) *Attorney, Agent, or Firm* — Tarolli, Sundheim, Covell & Tummino LLP

(57) ABSTRACT

An apparatus for vitrifying a biological specimen includes a cap member, a tubular plunger, and a specimen chamber. The cap member includes a stem portion integrally formed with a receiving portion. The receiving portion has a disc-like shape and includes an outer surface. The outer surface includes a first skirt member comprised of a heat-sealable material. The first skirt member is attached along a circumferential portion of the outer surface. The specimen chamber has an open first end portion, a closed second end portion, and a cavity extending between the first and second end portions. The cavity is defined by oppositely disposed inner and outer surfaces. The specimen chamber further includes a second skirt member comprised of heat-sealable material. The second skirt member is attached along a circumferential portion of the outer surface.

17 Claims, 25 Drawing Sheets

U.S. PATENT DOCUMENTS

| | | | |
|---|---|---|---|
| 7,353,721 B2 * | 4/2008 | Feller | 73/864.51 |
| 2002/0059802 A1 | 5/2002 | Lang | |
| 2002/0079318 A1 * | 6/2002 | Wurzinger | 220/592.01 |

FOREIGN PATENT DOCUMENTS

| | | |
|---|---|---|
| WO | WO-03/024213 A1 | 3/2003 |
| WO | WO-2006/007711 A1 | 1/2006 |
| WO | WO-2006/012613 A1 | 2/2006 |
| WO | WO 2007/093978 A1 | 8/2007 |

OTHER PUBLICATIONS

Baudot et al., "Towards Whole Sheep Ovary Cryopreservation", *Cryobiology*, Dec. 2007; 55(3): 236-48 (Abstract only).

Courbiere et al., "Cryopreservation of the Ovary by Vitrification as an Alternative to Slow-Cooling Protocols", *Fertil. Steril.*, Oct. 2006; 86 Suppl 4:1243-51.

International Search Report dated Nov. 2, 2010 for PCT International Application No. PCT/US2009/047815, filed Jun. 18, 2009 (4 pgs.).

* cited by examiner

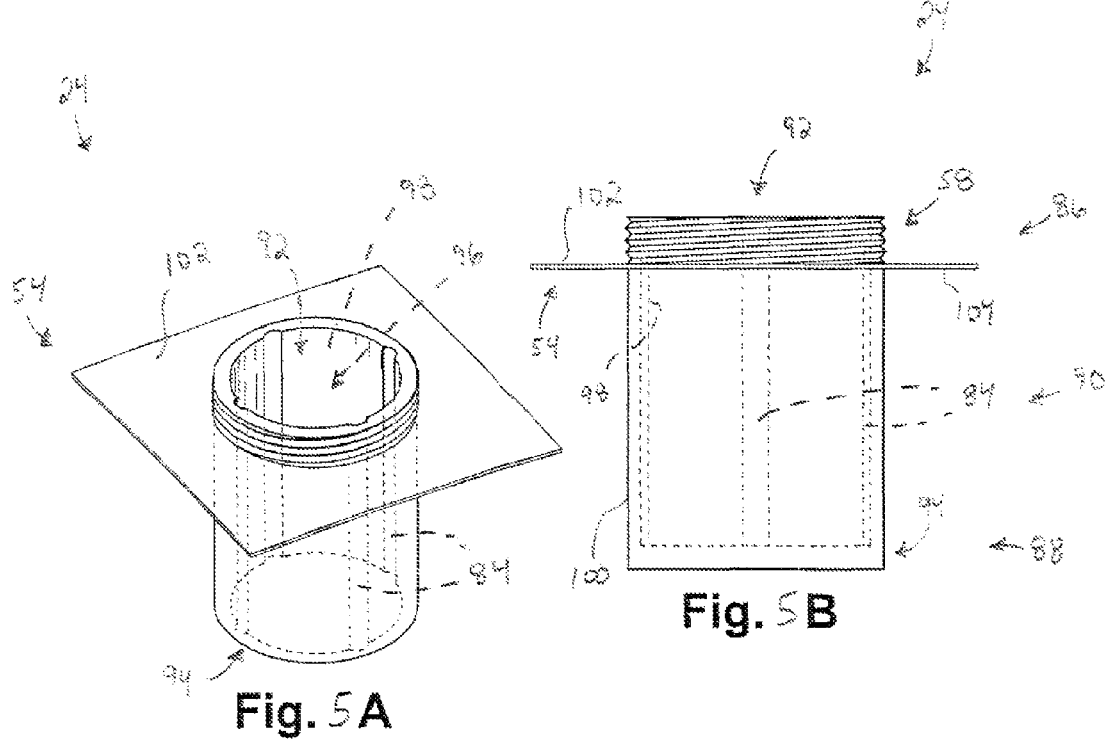

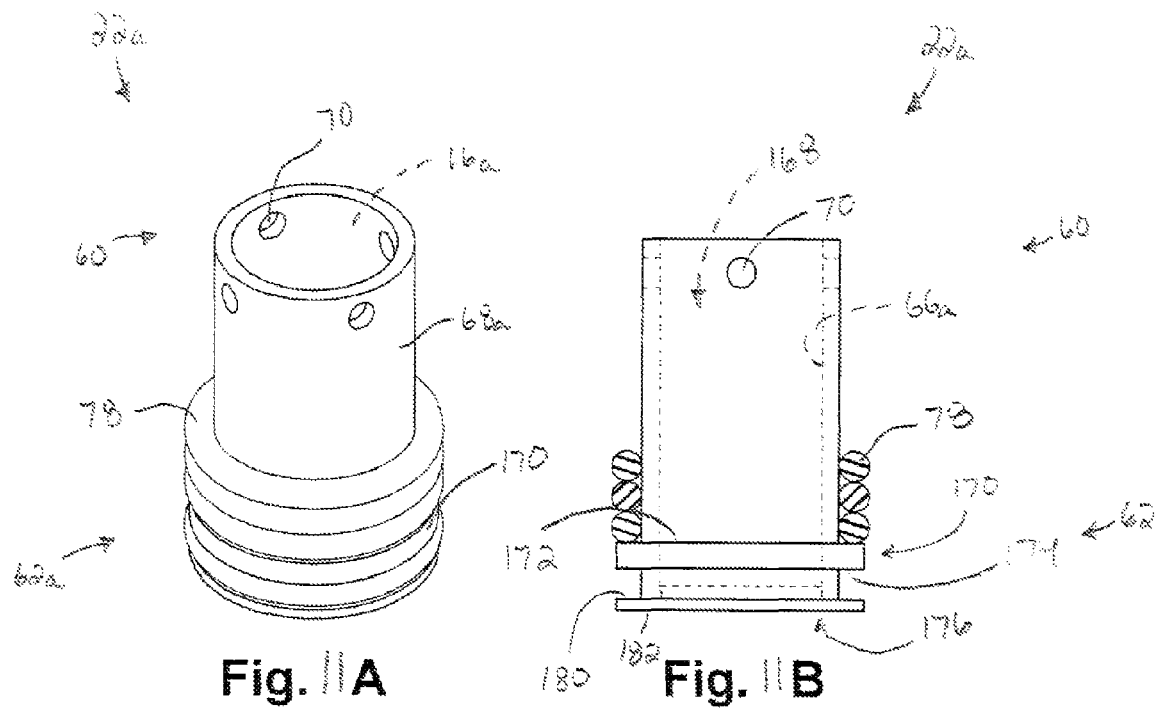
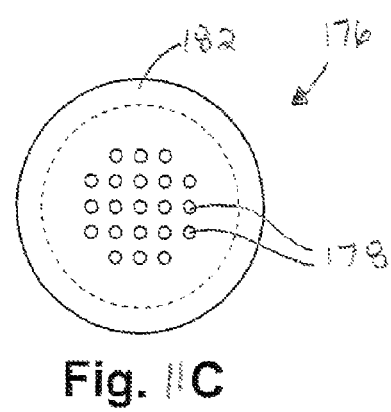
Fig. 11A  Fig. 11B
Fig. 11C

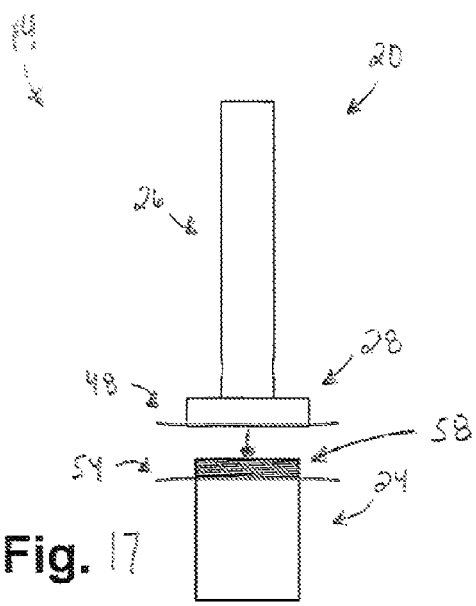
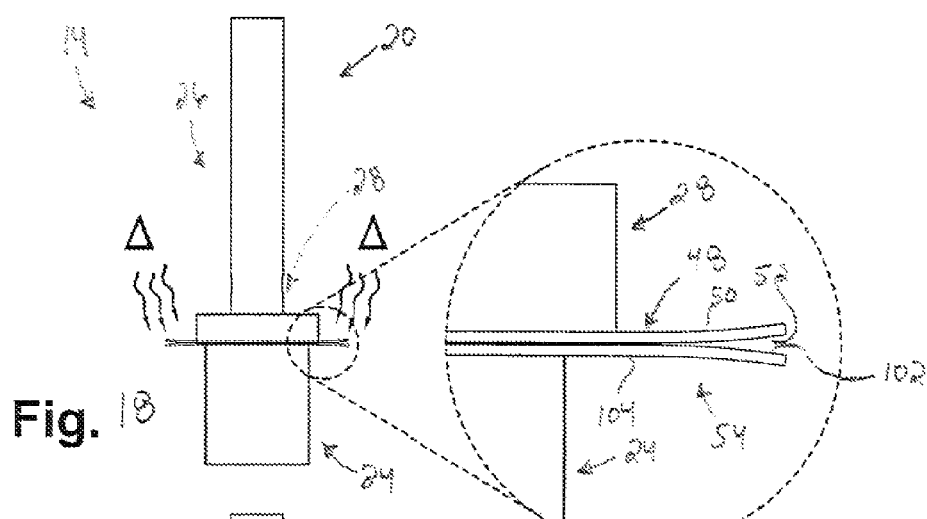
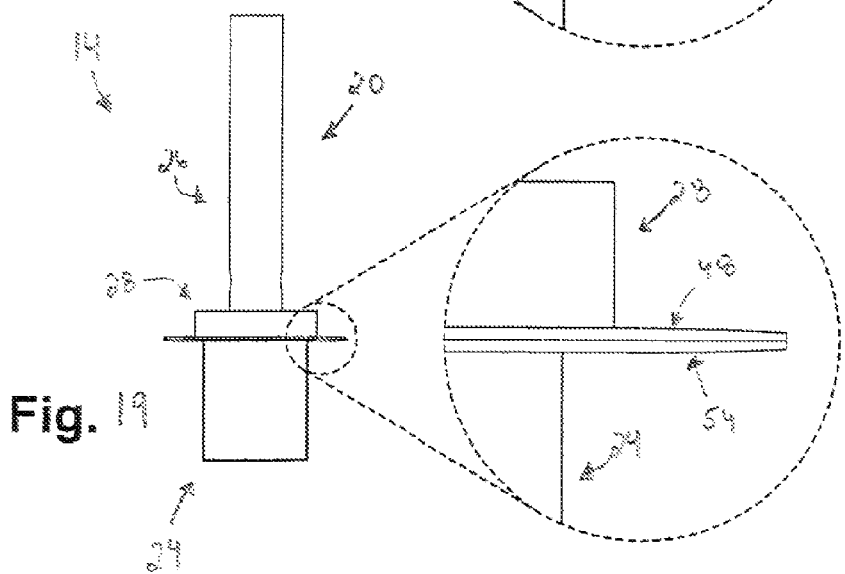

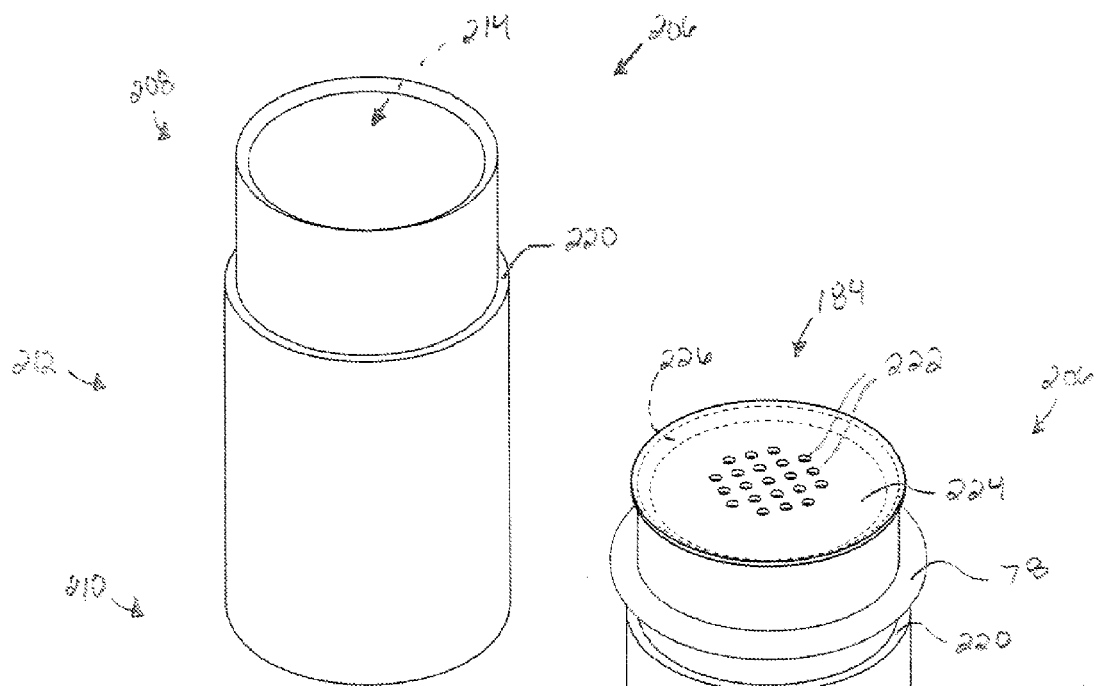
Fig. 24
Fig. 26
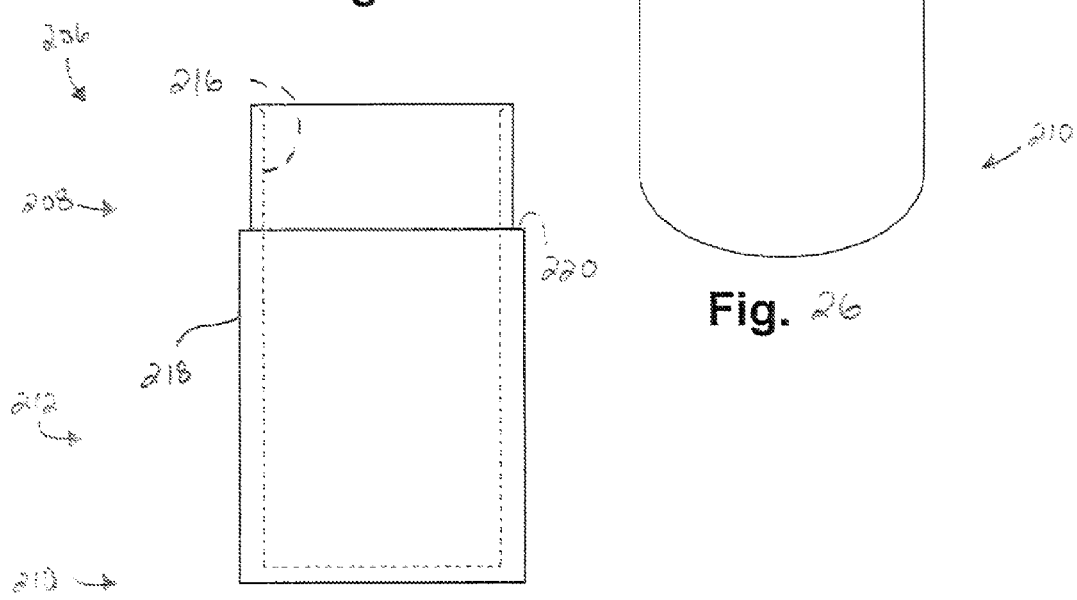
Fig. 25

SYSTEMS AND METHODS FOR VITRIFYING TISSUE

RELATED APPLICATION

This application claims priority from U.S. Provisional Patent Application Ser. No. 61/073,392, filed Jun. 18, 2008, the subject matter of which is incorporated hereby incorporated by reference in its entirety.

TECHNICAL FIELD

The present invention relates generally to systems and methods for cryogenic preservation, and more particularly to systems and methods for vitrifying biological specimens, such as single cells, cell clumps, cell suspensions, tissues, and tissue fragments.

BACKGROUND OF THE INVENTION

Vitrification is a relatively new approach for cryopreserving biological tissue. Vitrification addresses many of the problems associated with traditional, slow freezing techniques. For example, vitrification avoids cellular damage caused by ice crystal formation, eliminates the need for expensive programmable freezers, and reduces the long period of time needed to complete conventional cryopreservation programs.

The use of vitrification in the clinical setting has broadened with increasing success of the technique using standardized protocols for different cell types. For example, vitrification is currently finding use in the field of reproductive medicine as a means for vitrifying oocytes, embryos and blastocysts. Great successes and improvements in vitrifying these cell types are currently being made.

One important limitation to vitrification techniques is that very rapid heat transfer is needed to effectively cryopreserve tissue. The need for rapid heat transfer requires that vitrification devices be minimally-sized and capable of holding only small tissue volumes. Additionally, the amount of time that a biological tissue sample is exposed to cryoprotectants must be optimized to prevent cyotoxic effects.

Therefore, currently available vitrification devices are optimized for microscopic manipulation of a small number of cells prior to transfer into microvolume devices. Experiments using conventional carriers thus often fail to effectively cryopreserve large tissue volumes or cell suspensions. Effective tissue vitrification requires relatively short but adequate exposure to high concentration of cryoprotectants, ultra-rapid heat transfer during freezing and thawing, and rapid removal of the cryoprotectants immediately after thawing.

SUMMARY OF THE INVENTION

According to one aspect of the present invention, an apparatus for vitrifying a biological specimen comprises a cap member, a tubular plunger, and a specimen chamber. The cap member includes a stem portion integrally formed with a receiving portion. The receiving portion has a disc-like shape and includes an outer surface. The outer surface includes a first skirt member comprised of a heat-sealable material. The first skirt member is attached along a circumferential portion of the outer surface. The specimen chamber has an open first end portion, a closed second end portion, and a cavity extending between the first and second end portions. The cavity is defined by and oppositely disposed inner and outer surfaces. The specimen chamber further includes a second skirt member comprised of heat-sealable material. The second skirt member is attached along a circumferential portion of the outer surface.

According to another aspect of the present invention, a system for vitrifying a biological specimen comprises an apparatus for vitrifying the specimen and an applicator. The apparatus comprises a cap member, a tubular plunger, and a specimen chamber. The cap member includes a stem portion integrally formed with a receiving portion. The receiving portion has a disc-like shape and includes an outer surface. The outer surface includes a first skirt member comprised of a heat-sealable material. The first skirt member is attached along a circumferential portion of the outer surface. The specimen chamber has an open first end portion, a closed second end portion, and a cavity extending between the first and second end portions. The cavity is defined by oppositely disposed inner and outer surfaces. The specimen chamber further includes a second skirt member comprised of heat-sealable material. The second skirt member is attached along a circumferential portion of the outer surface. The applicator is for inserting and withdrawing the plunger from the specimen chamber. The applicator comprises a mating portion, a handle portion, and a main body portion extending between the mating portion and the handle portion.

According to yet another aspect of the present invention, a method is provided for vitrifying a biological specimen. One step of the method includes providing an apparatus comprising a cap member, a plunger, and a specimen chamber. The cap member comprises a stem portion integrally formed with a receiving portion. A first end portion of the plunger includes a plurality of openings extending between inner and outer surfaces. The specimen chamber has an open first end portion and a closed second end portion. The cap member and the specimen chamber respectively include first and second skirt members made of a heat-sealable material. Each of the first and second skirt members is respectively attached to an outer surface of the cap member and an outer surface of the specimen chamber. The specimen is placed in the specimen chamber, followed by addition of a vitrification solution into the specimen chamber. Next, the plunger is inserted into the specimen chamber. The receiving portion of the cap member is then mated with the first end portion of the specimen chamber. Next, a cooling fluid is applied to the apparatus to vitrify the specimen.

According to another aspect of the present invention, a method is provided for vitrifying a biological specimen. One step of the method includes providing an apparatus comprising a cap member, a plunger, and a specimen chamber. The cap member comprises a stem portion integrally formed with a receiving portion. The specimen chamber has an open first end and a closed second end. The cap member and the specimen chamber respectively include first and second skirt members made of a heat-sealable material. Each of the first and second skirt members is respectively attached to an outer surface of the cap member and an outer surface of the specimen chamber. The plunger comprises a channel that extends between first and second end portions and is defined by inner and outer surfaces. The first end portion of the plunger includes a plurality of openings extending between the inner and outer surfaces. The second end portion of the plunger includes a ridge that extends circumferentially about the outer surface and a filtering member extending substantially perpendicular to the channel. The biological specimen is placed in the specimen chamber, followed by insertion of the plunger into the specimen chamber. The first open end of the specimen chamber is then mated with the receiving portion of the cap member. Next, a cooling fluid is applied to the apparatus to vitrify the biological specimen.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 5A is a perspective view of the specimen chamber in FIG. 2A;

FIG. 5B is a cross-sectional view of the specimen chamber in FIG. 5A;

FIG. 5C is a top plan view of the specimen chamber in FIG. 5B;

FIG. 11A is a perspective view of the plunger in FIG. 10A;

FIG. 11B is a cross-sectional view of the plunger in FIG. 11A;

FIG. 11C is a bottom plan view showing a filtration member of the plunger in FIG. 11B;

FIG. 17 is a cross-sectional view showing the cap member of FIG. 2A being mated with the specimen chamber;

FIG. 18 is a cross-sectional view showing heat (Δ) being applied to first and second skirt members respectively attached to the cap member and the specimen chamber;

FIG. 19 is a cross-sectional view showing the first and second skirt members of FIG. 18 bonded or sealed together;

FIG. 24 is a perspective view showing a sealing member applicator;

FIG. 25 is a cross-sectional view of the sealing member applicator in FIG. 24;

FIG. 26 is a perspective view showing a disposable filter positioned atop the sealing member applicator in FIG. 24;

DETAILED DESCRIPTION

Figure 1:
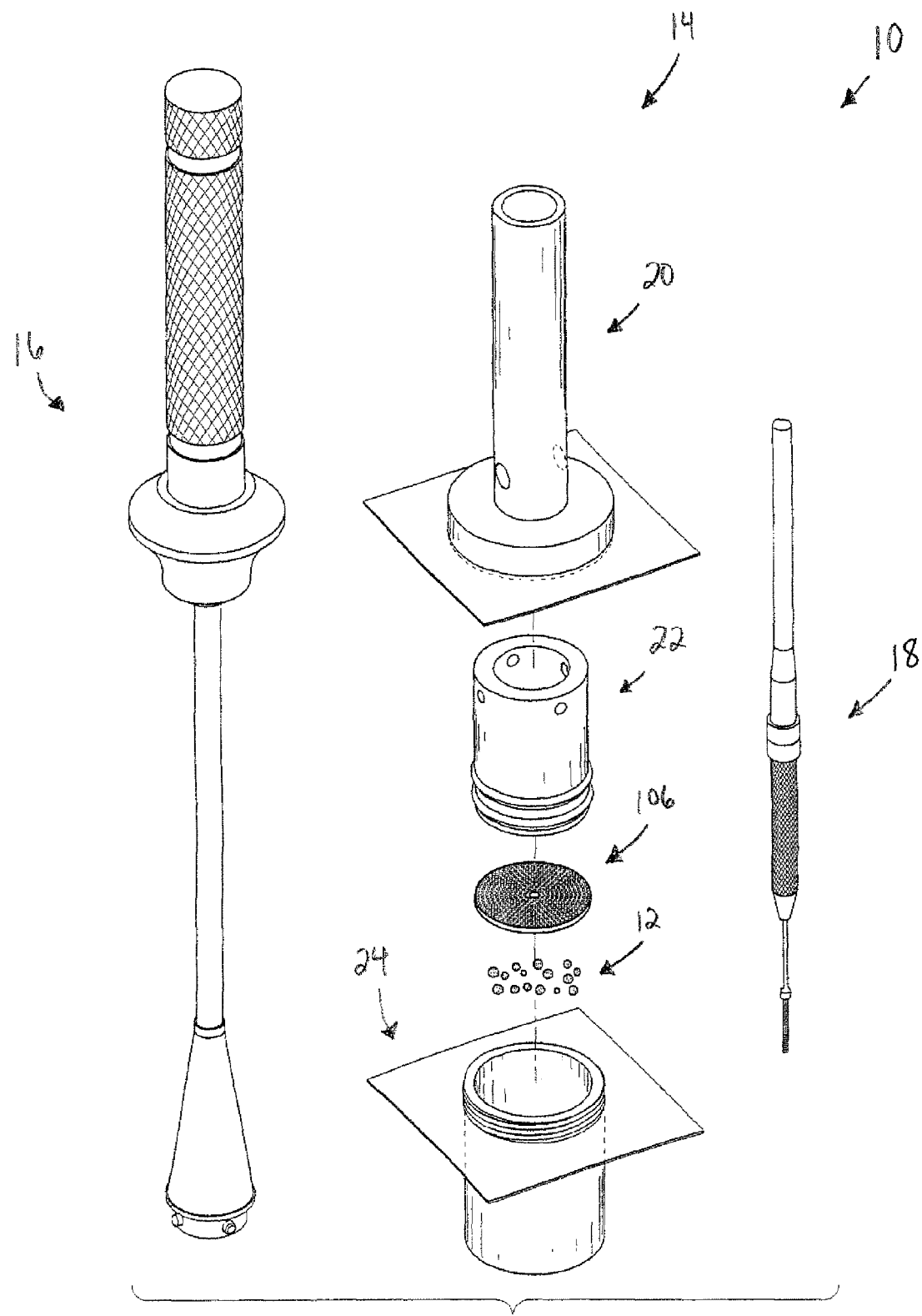
FIG. 1 is a perspective view showing a system for vitrifying a biological specimen comprising an applicator, an apparatus (exploded configuration), and a removal tool according to one aspect of the present invention.
Figure 9:
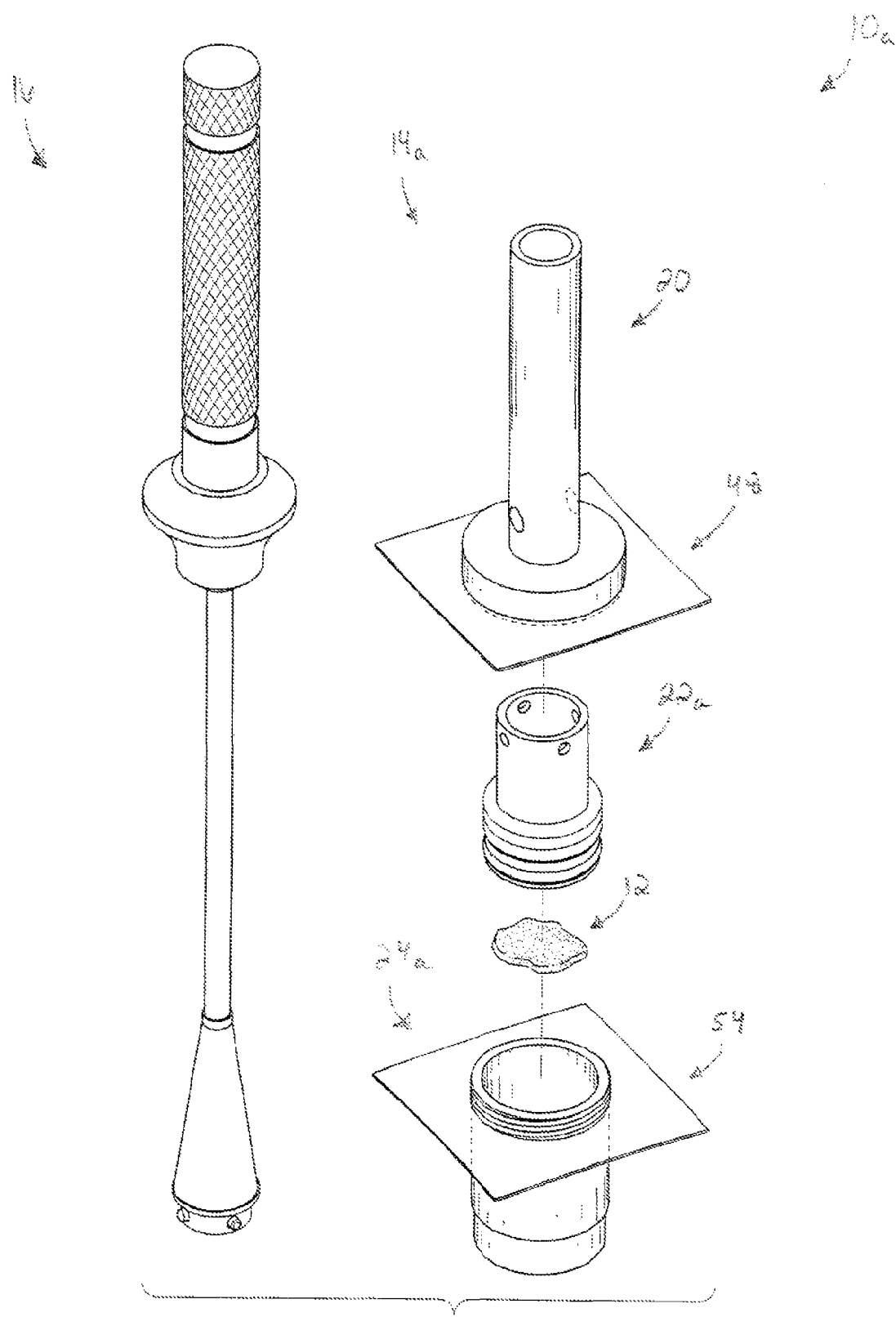
FIG. 9 is a perspective view showing a system for vitrifying a biological specimen comprising an applicator and an apparatus (exploded configuration) according to another aspect of the present invention.
Figures 10A, 10B:
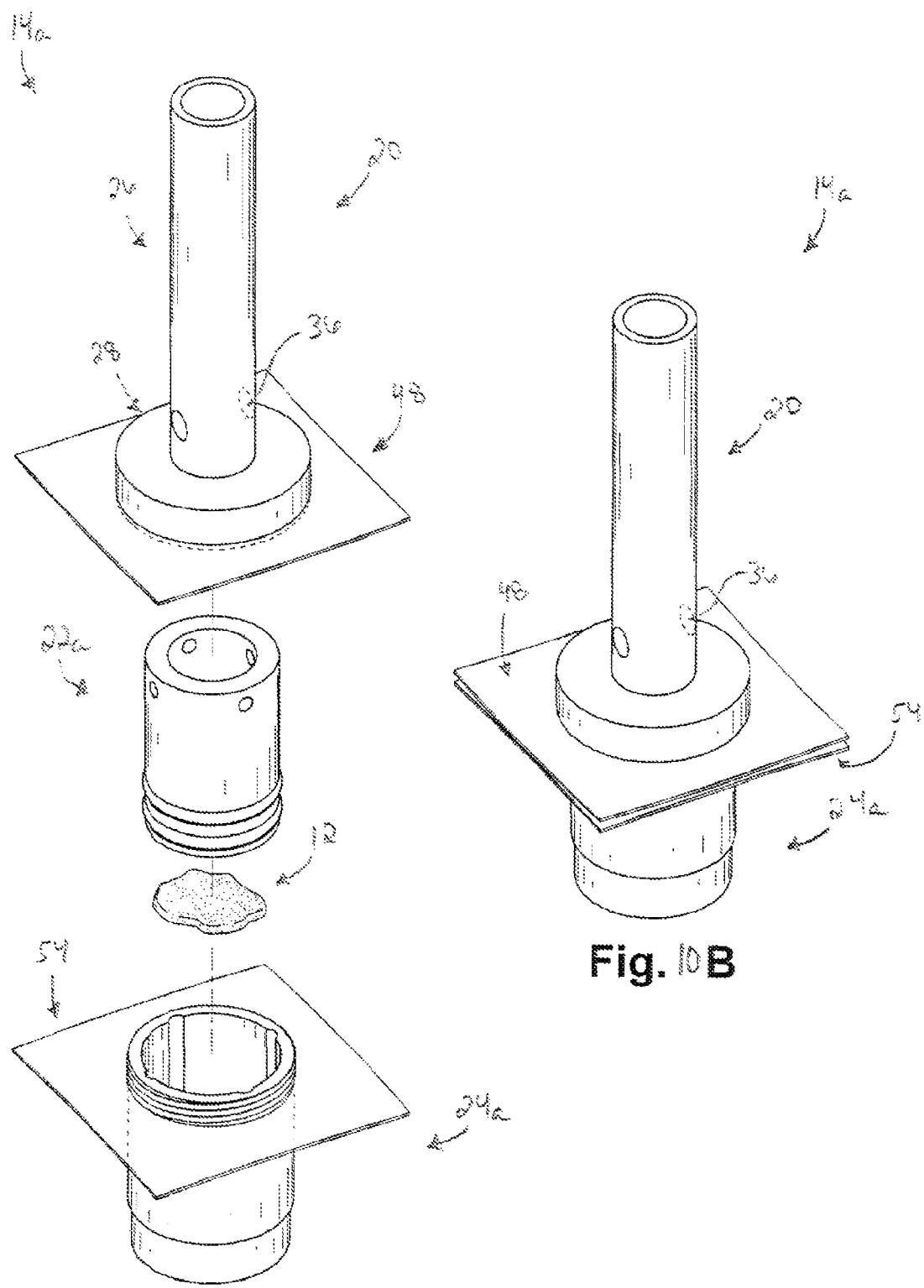
FIG. 10A is an exploded perspective view showing an alternative configuration of the apparatus in FIG. 2A for vitrifying a biological specimen, the apparatus comprising a cap member, a plunger, and a specimen chamber.
FIG. 10B is a perspective view showing the apparatus in FIG. 10A in an assembled configuration.

The present invention relates generally to systems and methods for cryogenic preservation, and more particularly to systems and methods for vitrifying biological specimens, such as single cells, cell clumps, cell suspensions, tissues, and tissue fragments. As representative of the present invention, FIGS. 1 and 9 illustrate systems 10 and $10_a$ for vitrifying biological specimens 12. Unlike vitrification systems of the prior art, which produce only surface vitrification when used with large volumes of biological tissue, the present invention represents a closed vitrification system capable of accommodating a relatively large volume of biological tissue without compromising the principles of vitrification by allowing rapid, even distribution of temperature. Although the present invention is described below in the context of vitrifying an ovarian tissue sample, it will be appreciated that any one or combination of biological tissue types can be vitrified using the present invention.

Unless otherwise defined, all technical terms used herein have the same meaning as commonly understood by one of ordinary skill in the art to which the present invention pertains.

In the context of the present invention, the term "cooling fluid" can refer to any material including, but not limited to, liquid gases, such as liquid nitrogen, liquid propane, liquid isopentane, liquid helium or ethane slush, which are capable of causing vitrification of a biological specimen.

As used herein, the term "cryopreservation" can refer to the preservation of a biological specimen at extremely low temperature.

As used herein, the terms "vitrification" or "vitrify" can refer to a phenomenon whereby a biological specimen is rapidly cooled to very low temperatures, such that the tissue forms a glass-like state without undergoing crystallization.

As used herein, the term "biological specimen" can refer to any sort of viable living cell, cell aggregate, cell suspension, tissue, or tissue fragment. Biological specimens can include mammalian developmental cells, such as sperm, embryos, blastocysts, morulae and oocytes. Biological specimens can be derived from any desired mammalian source including, but not limited to, humans, non-human primates (e.g., monkeys), laboratory mammals (e.g., rats, mice and hamsters), agricultural livestock (e.g., pigs, sheep, cows, goats and horses), and zoologically important and/or endangered animals. Biological specimens can be processed or unprocessed, and can be continuous or discontinuous biological material. The use of other developmental cells from other living creatures, such as reptiles, amphibians, and insects (e.g., *Drosophila*) is also within the scope of the present invention. Other suitable biological specimens for use with the present invention include stem cells, including human stem cells, and plant tissue cells.

As used herein, the term "viable" can mean that the biological specimen comprises some viable cells or tissue that are/is metabolically active or would become metabolically active after their release from a cryopreserved state. Viability may be assessed according to any applicable method known in the art (e.g., a live/dead ratio assay). Release from the preservation state may be through any protocol that should be chosen to suit the method of cryopreservation and the nature of the biological specimen by, for example, rapidly warming the biological specimen and using one or more types of media to remove cryoprotectants added before vitrification and allow rehydration. Alternatively, a viable biological specimen can mean that upon release from a cryopreserved state, the preserved biological specimen substantially restores its normal function.

As used herein, the term "cryoprotectant" can refer to a chemical that minimizes ice crystal formation in a biological specimen when the specimen is cooled to subzero temperatures and results in an increase in viability after warming.

As used herein, the term "base medium" can refer to a solid or liquid preparation made specifically for the growth, manipulation, transport, or storage of a biological specimen present therein.

Figures 2A, 2B:
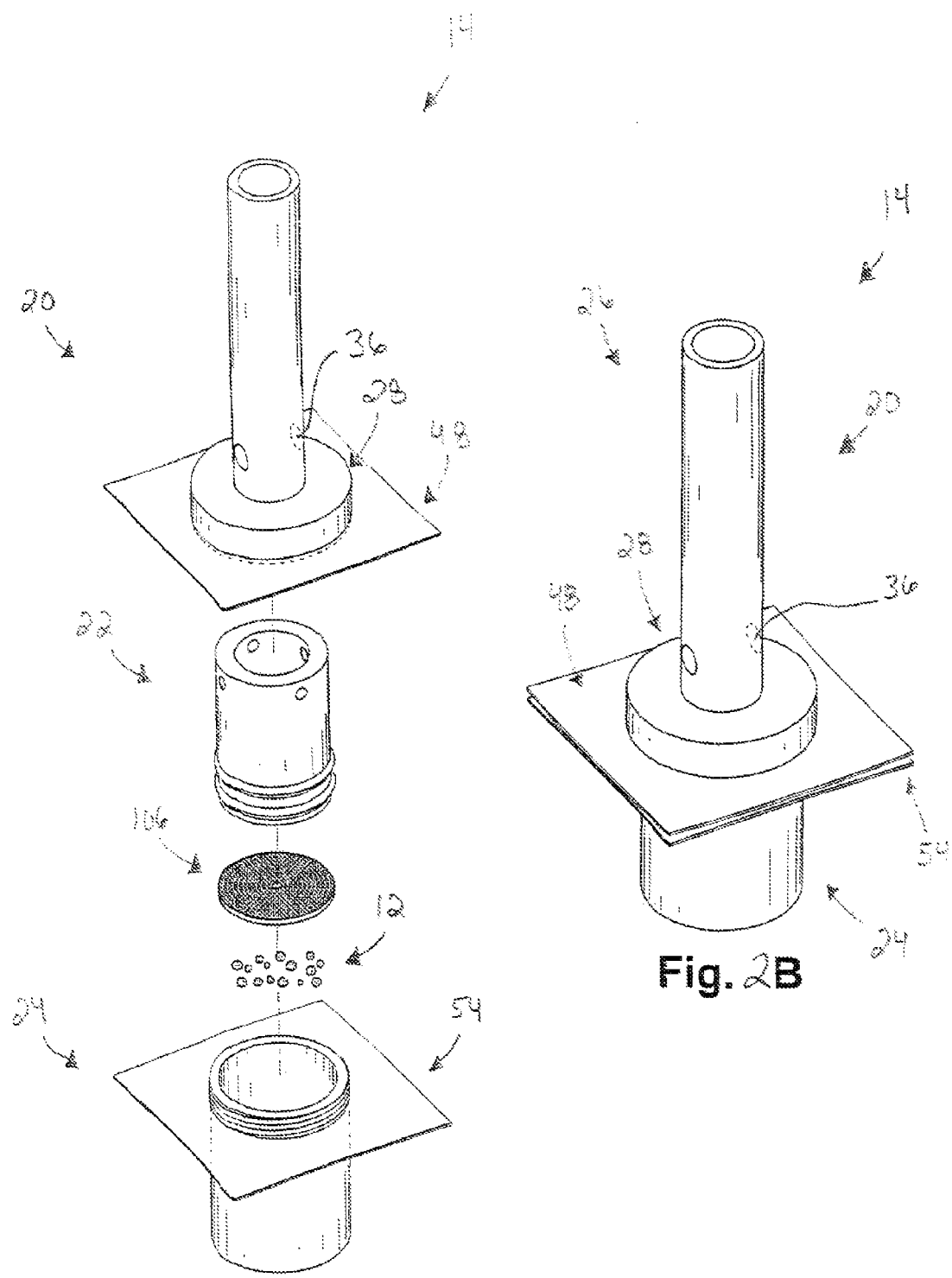
FIG. 2A is an exploded perspective view showing an apparatus (FIG. 1) for vitrifying a biological sample comprising a cap member, a plunger, a specimen holder, and a specimen chamber.
FIG. 2B is a perspective view showing the apparatus in FIG. 2A in an assembled configuration.

Referring again to FIG. 1, one aspect of the present invention includes a system 10 for vitrifying a biological specimen 12. The system 10 comprises a vitrification apparatus 14, an applicator 16, and a removal tool 18. As shown in FIGS. 2A-B, the apparatus 14 comprises a cap member 20, a plunger 22, and a specimen chamber 24. The cap member 20 (FIGS. 3A-B) includes a stem portion 26 integrally formed with a receiving portion 28. The cap member 20 can be made of a rigid metallic or non-metallic material including, but not limited to, polished aluminum, stainless steel, titanium, titanium alloy, or hardened plastic. It will be appreciated that the stem portion 26 can additionally or alternatively be made of concrete or a non- or low-heat conductive material.

Figure 3A:
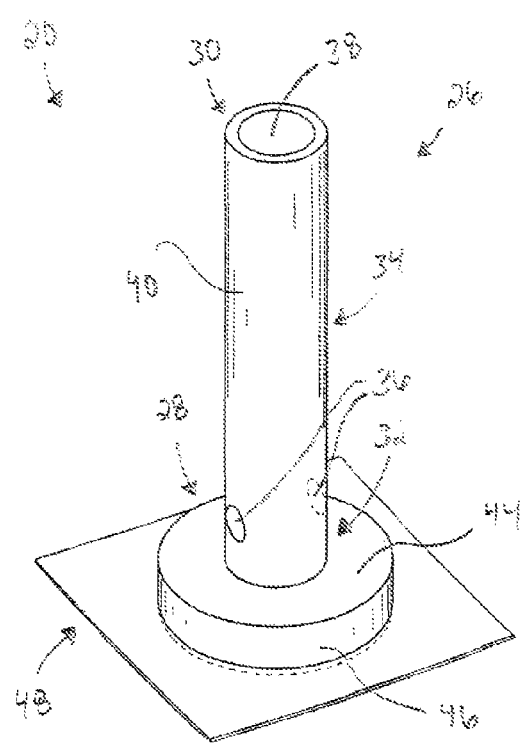
FIG. 3A is a perspective view of the cap member in FIG. 2A.
Figure 3B:
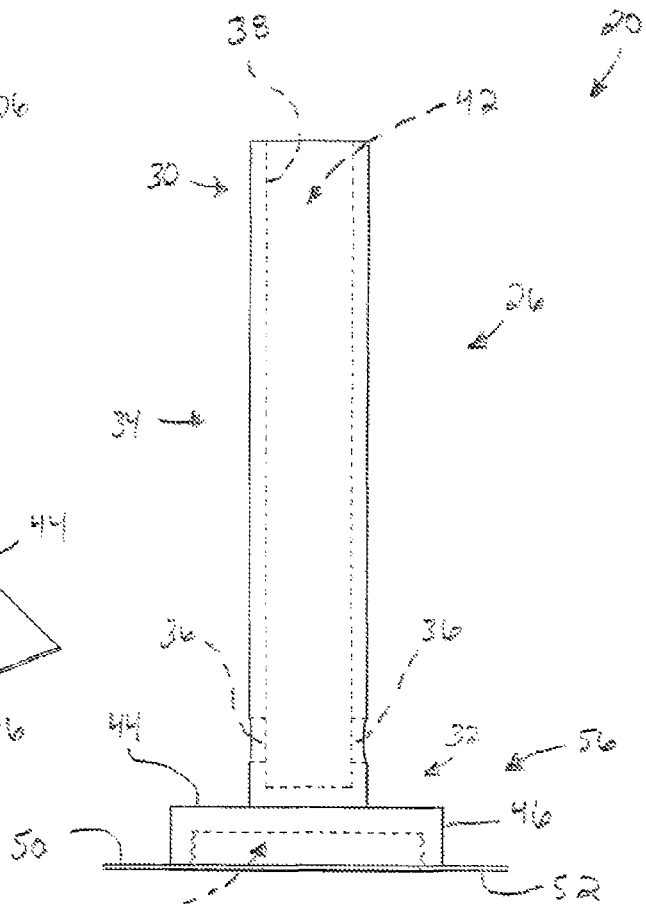
FIG. 3B is a cross-sectional view of the cap member in FIG. 3A.

As shown in FIGS. 3A-B, the stem portion 26 has a tubular configuration and includes a first end portion 30, a second end portion 32, and a main body portion 34 extending between the end portions. The second end portion 32 of the stem portion 26 includes a plurality of oppositely disposed openings 36, each of which extends between an inner surface 38 and an outer surface 40. Each of the openings 36 is in fluid communication with a cavity 42 that extends between the first and second end portions 30 and 32.

The openings 36 (FIGS. 3A-B) provide a means for a cooling or warming fluid to rapidly enter and exit the cap member 20 when the apparatus 14 (FIGS. 2A-B) is being cooled or warmed (respectively). Any thermal effect of the cap member 20 (FIGS. 3A-B) is terminated when the cap member is unscrewed after warming. Although the stem portion 26 is illustrated with two openings 36, it will be appreciated that the stem portion can include any desired number and location of openings. Additionally. it will be appreciated that the shape of the openings 36 can be circular as shown in FIGS. 3A-B or, alternatively, any other desired shape, such as square, ovoid, rectangular, etc.

The receiving portion 28 of the cap member 20 has a disc-like configuration and includes a major surface 44 extending substantially perpendicular to the second end portion 32 of the stem portion 26. The receiving portion 28 additionally comprises a minor outer surface 46 that extends substantially perpendicular to the major surface 44. Although not illustrated in FIG. 3A, it will be appreciated that all or only a portion of the minor outer surface 46 can be textured to improve handling of the receiving portion 28 (e.g., screwing the cap member 20 onto the specimen chamber 24).

As shown in FIGS. 3A-B, the receiving portion 28 of the cap member 20 also includes a first skirt member 48 attached along a circumferential portion of, and extending substantially radial to, the minor outer surface 46. The first skirt member 48 comprises a layer or sheet of a heat-sealable material (e.g., polyethylene) having a first surface 50 oppositely disposed from a second surface 52. The first skirt member 48 is securely attached along the circumferential portion of the minor outer surface 46 via an adhesive or other bonding substance (not shown). Although the first skirt member 48 is shown as having a thin, square-like configuration in FIGS. 3A-B, it will be appreciated that the first skirt member can have any shape (e.g., circular, rectangular) and thickness. As described in more detail below, the first skirt member 48 can be heat-bonded to a second skirt member 54 (FIGS. 5A-C) to form a fluid-tight seal capable of preventing fluid leakage into or out of the specimen chamber 24.

The receiving portion 28 (FIG. 3B) also includes a recess 56 for. receiving the specimen chamber 24 (FIG. 2A). Although not shown in detail, the recess 56 (FIG. 3B) includes an inner threaded portion for mating with a threaded portion 58 (FIG. 5A) of the specimen chamber 24. It will be appreciated that the inner threaded portion (FIG. 3B) of the recess 56 can include other means to facilitate mating with the threaded portion 58 (FIG. 5A) of the specimen chamber 24, such as a rubber gasket (not shown) or the like.

Figure 4A:
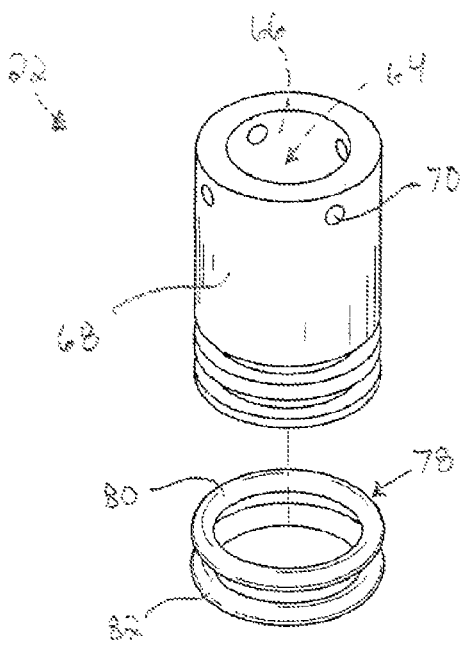
FIG. 4A is an exploded perspective view of the plunger in FIG. 2A.
Figure 4B:
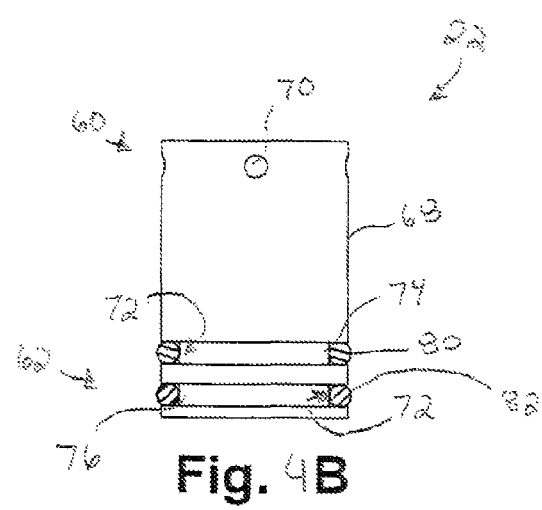
FIG. 4B is a cross-sectional view of the plunger shown in FIG. 4A.
Figure 4C:
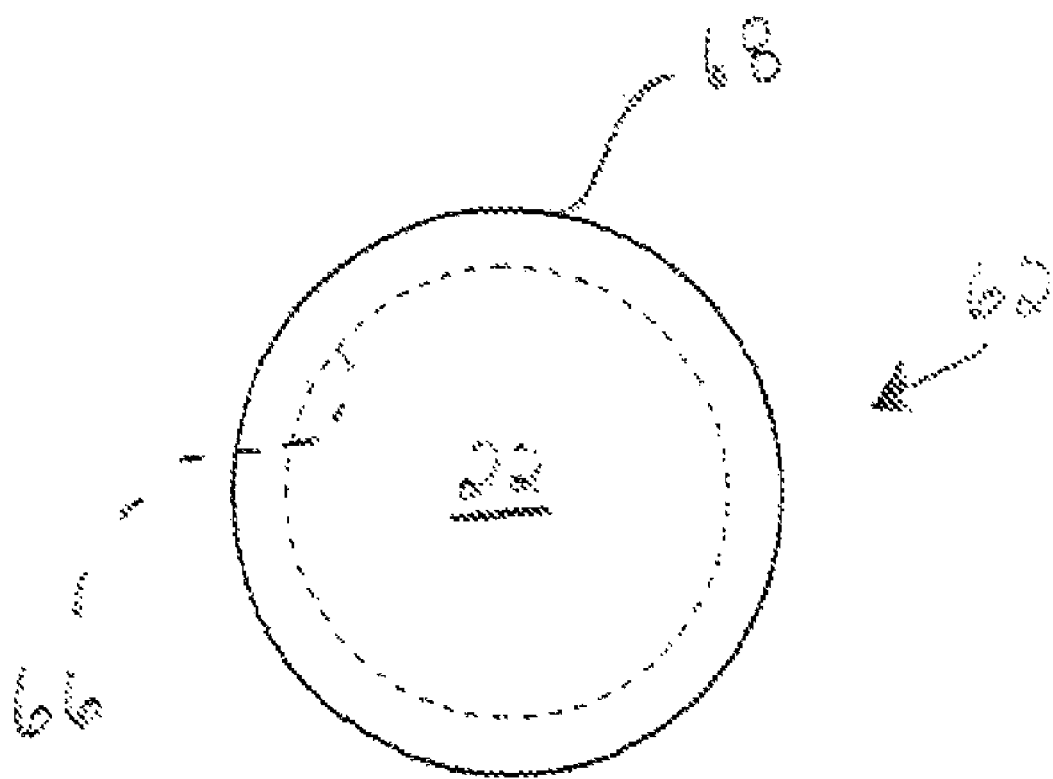
FIG. 4C is a plan view showing the bottom of the plunger in FIG. 4A.

Referring to FIGS. 4A-C, the plunger 22 has a tubular configuration and includes an open first end portion 60, a closed second end portion 62, and a cavity 64 extending between the first and second end portions. The cavity 64 of the plunger 22 is defined by an inner surface 66 and an outer surface 68. The plunger 22 has a versatile construction to tolerate pressure changes and frictional forces. The plunger 22 can be made of any rigid or semi-rigid material, such as a hardened plastic (e.g., polystyrene, polyethylene or polyvinylchloride), metal, or metal alloy. The plunger 22 can be reusable or, alternatively, may be disposable after each use.

As described in more detail below, the plunger 22 is dimensioned to snugly fit inside the specimen chamber 24.

The first end portion 60 of the plunger 22 includes four oppositely disposed openings 70, each of which extends between the inner and outer surfaces 66 and 68. As shown in FIGS. 4A-B, each of the openings 70 is oppositely spaced apart, and about equally spaced around, the first end portion 60. As described in more detail below, the openings 70 facilitate positioning of the plunger 22 in the specimen chamber 24 (FIG. 2A). It will be appreciated that any number of openings 70 (FIGS. 4A-B), having any desired shape, size, and location (relative to one another) may be disposed at the first end portion 60 of the plunger 22. Additionally, it will be appreciated that the plunger 22 may not include any openings 70, and that handling the plunger can instead be accomplished using an appropriate tool, such as pliers (not shown) or tweezers (not shown).

The second end portion 62 of the plunger 22 includes at least one groove 72 that extends circumferentially about the outer surface 68. The size, number, and position of the at least one groove 72 can be varied as needed. As shown in FIG. 4B, for example, the plunger 22 can include a first groove 74 spaced apart from a second groove 76. It should be appreciated that the plunger 22 can include fewer or greater than two grooves 72, and that the grooves can be located elsewhere about the plunger 22 (e.g., at or near the first end portion 60).

Each of the grooves 72 includes at least one sealing member 78 operably secured therein. As shown in FIGS. 4A-B, first and second sealing members 80 and 82 comprising rubber O-rings can be friction fit into the first and second grooves 74 and 76, respectively. The at least one sealing member 78 prevents or mitigates leakage of a media solution during operation of the apparatus 14 so that applied pressure when moving the plunger 22 drives any excess media through the specimen chamber 24 (via the longitudinal grooves 84 shown in FIGS. 5A-C) for subsequent removal. It will be appreciated that other types of sealing members 78, such as a removable adhesive tape (not shown) can alternatively be used. Additionally, it will be appreciated that the at least one sealing member 78 can be integrally formed with the at least one groove 72, and that the size and shape of the at least one sealing member can be varied as needed.

The specimen chamber 24 (FIGS. 5A-C) has a cup-like shape for receiving the biological specimen 12 and the plunger 22. As shown in FIGS. 5A-B, the specimen chamber 24 comprises an open first end portion 86, a closed second end portion 88, and a main body portion 90 extending between the first and second end portions. The first end portion 86 includes a first open end 92 and a threaded portion 58 (FIG. 3B) for mating with the inner threaded portion of the cap member 20. The second end portion 88 includes a second closed end 94. The specimen chamber 24 (FIG. 5A) also includes a cavity 96 that extends between the first and second end portions 86 and 88 and is defined by inner and outer surfaces 98 and 100.

The specimen chamber 24 can be made of a rigid metallic or non-metallic material that is highly temperature conductive, such as polished aluminum, stainless steel, titanium, titanium alloy, or hardened plastic. For example, the second closed end 94 of the specimen chamber 24 can be made of a thin layer (or layers) of a highly temperature conductive material, such as aluminum to facilitate heat transfer between the biological specimen 12 and a cooling fluid. Although not shown in FIGS. 5A-C, it will be appreciated that the second closed end 94 can have a thickness sufficient to support a plurality of axially-extending grooves to facilitate heat transfer.

The inner surface 98 of the specimen chamber 24 also includes at least one groove 84 that extends longitudinally between the first and second end portions 86 and 88. For example, the at least one groove 84 can extend entirely between the first open end 92 and the second closed end 94 of the specimen chamber 24. As shown in FIGS. 5A-C, the inner surface 98 of the specimen chamber 24 includes four, equally spaced apart grooves 84 that extend the entire distance between the first open end 92 and the second closed end 94. Although the grooves 84 illustrated in FIGS. 5A-C have a linear configuration and a semi-circular cross-sectional shape, it will be appreciated that the grooves can have any desired configuration (e.g., zigzag, serpentine, etc.) and cross-sectional shape (e.g., square-like, pyramidal). The groove(s) 84 facilitate insertion of the plunger 22 (FIG. 2A) into the specimen chamber 24 (FIGS. 5A-C) by allowing any air in the specimen chamber to travel upward through the groove(s) towards the first end portion 86 and thereby relieve the pressure applied by the plunger.

The first end portion 86 of the specimen chamber 24 also includes a second skirt member 54 constructed in a similar or identical manner as the first skirt member 48 (FIGS. 3A-B). The second skirt member 54 (FIGS. 5A-C) is attached along a circumferential portion of, and extends substantially radial to, the outer surface 100 at the first end portion 86 of the specimen chamber 24. The second skirt member 54 comprises a layer or sheet of a heat-sealable material (e.g., polyethylene) having a first surface 102 oppositely disposed from a second surface 104. The second skirt member 54 is securely attached along the circumferential portion of the outer surface 100 via an adhesive or other bonding substance (not shown). Although the second skirt member 54 is shown as having a thin, square-like configuration, it will be appreciated that the second skirt member can have any desired shape (e.g., circular, rectangular) and thickness.

Figure 6:
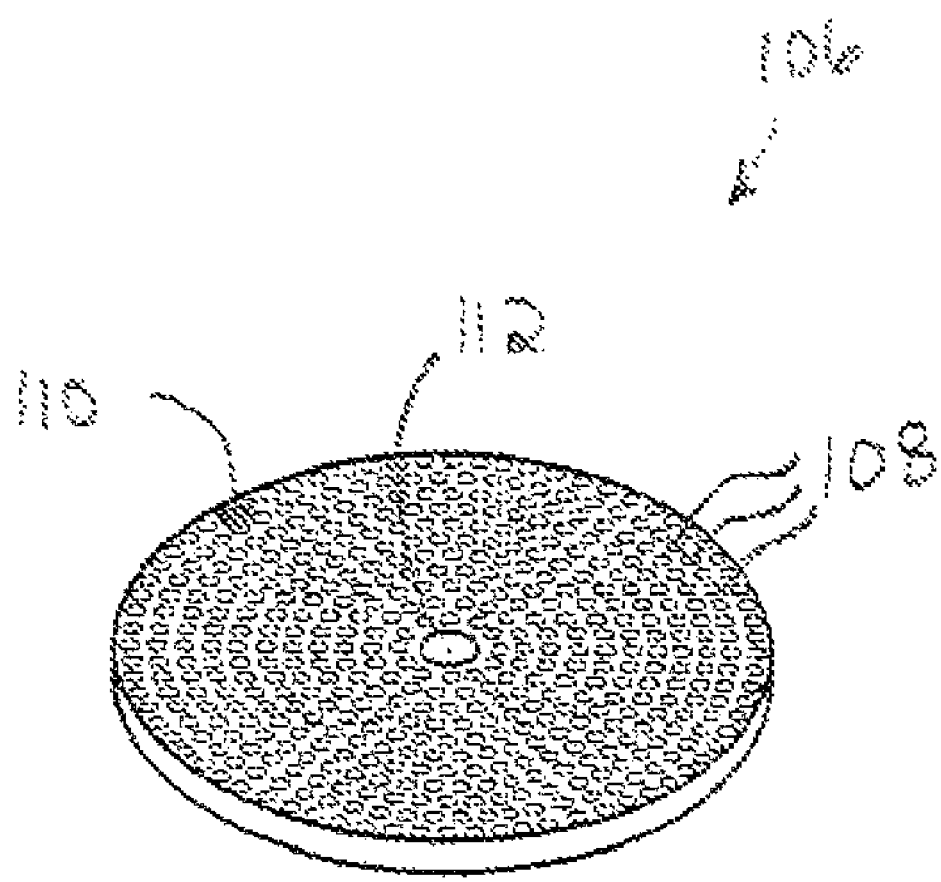
FIG. 6 is a perspective view of the specimen holder in FIG. 2A.

The system 10 (FIG. 1) can additionally or optionally include disc-shaped specimen holder 106 that is sufficiently sized to facilitate transport of the biological specimen 12 out of the specimen chamber 24, as well as to facilitate heat transfer between the specimen and the cooling fluid. As shown in FIG. 6, the specimen holder 106 has a flattened configuration and includes a plurality of pores 108 extending between a first surface 110 and an oppositely disposed second surface (not shown). The specimen holder 106 also includes a centrally-located mating aperture 112 extending between the first surface 110 and the second surface. Although not clearly shown in FIG. 6, the mating aperture 112 can be threaded. The specimen holder 106 can be made of any highly temperature conductive, rigid material (e.g., stainless steel) or semi-rigid material, such as a hardened plastic (e.g., polystyrene, polyethylene or polyvinylchloride). It will be appreciated that the specimen holder 106 can have any desired number of pores 108, and that the mating aperture 112 can be located elsewhere (i.e., not centrally) about the specimen holder.

Figure 7:
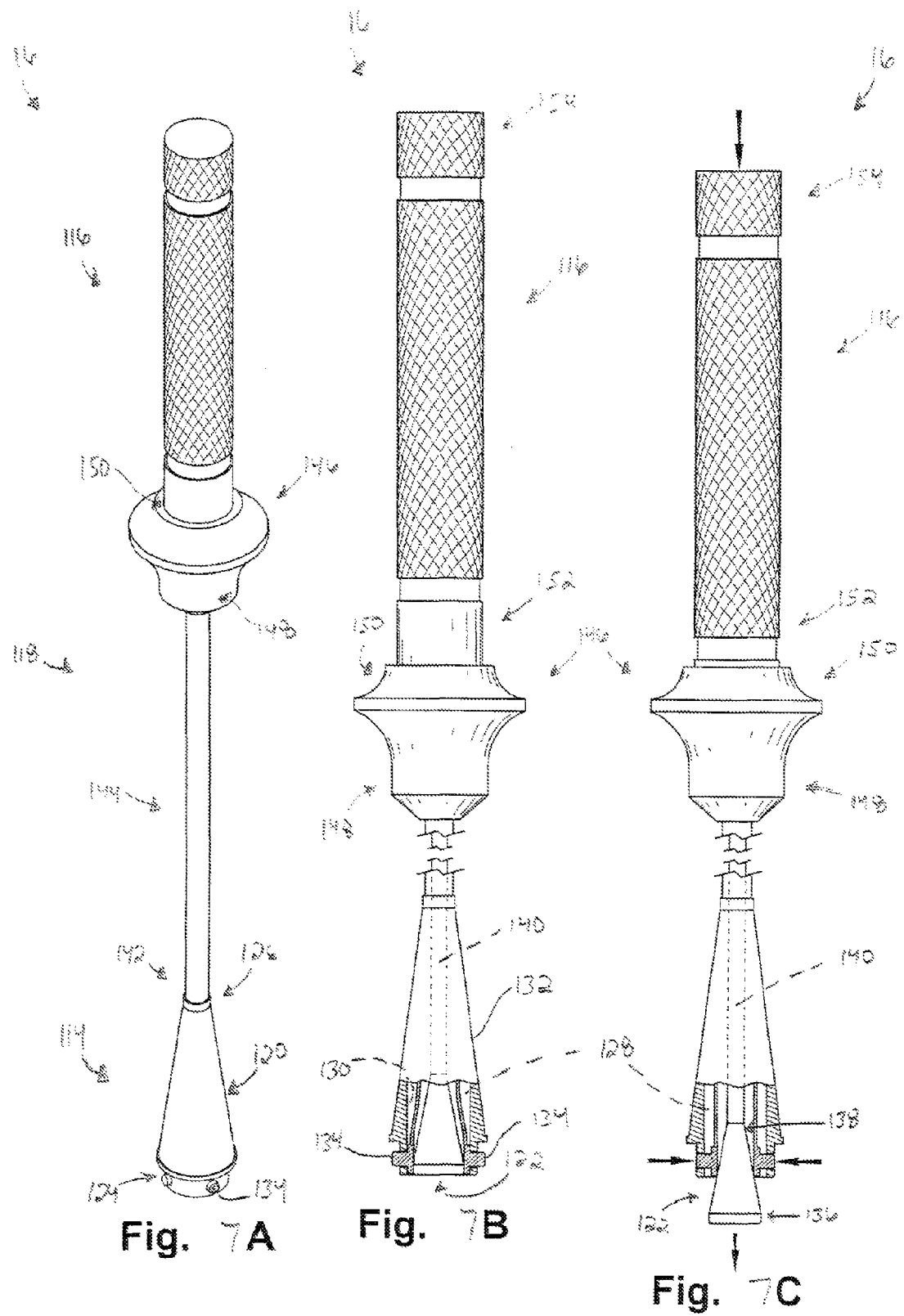
FIG. 7A is a perspective view of the applicator in FIG. 1.
FIG. 7B is a cross-sectional view of a mating portion of the applicator in FIG. 7A, the mating portion including an actuator member at least partially retained within a casing.
FIG. 7C is a cross-sectional view of the of the applicator in FIG. 7B showing the actuating member extending out of the casing.

The system 10 (FIG. 1) additionally comprises an applicator 16 (FIGS. 7A-C) for inserting and withdrawing the plunger 22 from the specimen chamber 24. The applicator 16 comprises a mating portion 114, a handle portion 116, and a main body portion 118 that extends between the mating portion and the handle portion. The applicator 16 can be made of one or more rigid materials, such as various medical grade metals or metal alloys (e.g., stainless steel, titanium, titanium alloys, etc.).

The mating portion 114 of the applicator 16 comprises a hollow casing 120 and an actuator member 122. The casing 120 has a conical or frusto-conical configuration and includes a first end portion 124, a second end portion 126, and a cavity 128 that extends between the first and second end portions. The cavity 128 is defined by an inner surface 130 and an outer surface 132. The first end portion 124 includes a plurality of retractable pins 134 that extend through apertures (not shown in detail) extending between the inner and outer surfaces 130 and 132. Each of the pins 134 extends substantially transverse to the actuator member 122. Additionally, each of the pins 134 is in contact with the actuator member 122 and can pivot transversely (with respect to the actuator member) through the apertures via tensioning mechanism (not shown in detail). The second end portion 126 of the casing 120 is integrally formed with the main body portion 118 of the applicator 16.

Referring to FIGS. 7B-C, the actuator member 122 has a conical or frusto-conical configuration and is movably disposed within the casing 120. The actuator member 122 includes a first end 136 having a diameter that is greater than the diameter of a second end 138. The diameter of the first end 136 is less than the diameter of the cavity 128 at the first end portion 60 (FIGS. 4A-B) of the plunger 22. The second end 138 (FIG. 7C) of the actuator member 122 is integrally formed with a control shaft 140. As described below, the control shaft 140 comprises part of an actuating mechanism (not shown in detail) used to slidably extend the actuator member 122 into the cavity 64 (FIGS. 4A-B) of the plunger 22.

The main body portion 118 (FIGS. 7A-C) of the applicator 16 has an elongated, tube-like configuration and includes a first end portion 142, a second end portion (not shown), and a central portion 144 extending between the end portions. The first end portion 142 is integrally formed with the second end portion 126 of the casing 120, and the second end portion is securely disposed within the handle portion 116. The control shaft 140 extends from the actuating member 122, through the central portion 144, and into the handle portion 116 where the control shaft is operably linked to a spring-loaded mechanism (not shown).

The central portion 144 includes a bell-shaped abutment member 146 that has first and second ends 148 and 150 and is slidably mounted to the central portion. The abutment member 146 is operably secured to the central portion 144 via a male/female threaded portion (not shown). As shown in FIGS. 7B-C, the second end 150 of the abutment member 146 is slidable over a first end 152 of the handle portion 116 when an axial force (e.g., using tactile means) is applied to the first end 148 of the abutment member. Application of the axial force causes the actuator member 122 to extend longitudinally from the casing 120 of the applicator 16 (FIG. 7C).

The handle portion 116 of the applicator 16 includes first and second ends 152 and 154. As indicated by the cross-hatched section in FIGS. 7A-C, the handle portion 116 includes a textured surface to facilitate handling of the applicator 16. The first end 152 includes an opening (not shown in detail) for receiving the central portion 144 of the main body portion 118. The first end 152 has a diameter that is less than the diameter of the second end 150 of the abutment member 122. This permits movement of the abutment member 122 over the first end 152 when a radial force is applied at the first end 148 of the abutment member.

The system 10 (FIG. 1) additionally comprises a removal tool 18 (FIG. 8) for transporting the biological specimen 12 out of the specimen chamber 24. The removal tool 18 comprises a mating end 158, a handle portion 160, and a middle portion 162 extending between the mating end and the handle portion. The removal tool 18 can be made of one or more rigid materials, such as various medical grade metals or metal alloys (e.g., stainless steel, titanium, titanium alloys, etc.).

The mating end 158 is integrally formed with the middle portion 162 and has a cross-sectional area that is less than the cross-section area of the middle portion. The mating end 158 includes a mating tip 164 configured to mate with the mating aperture 112 (FIG. 6) of the specimen holder 106. Where the mating aperture 112 of the specimen holder 106 is threaded, for example, at least a portion of the mating tip 164 (FIG. 8) can have a threaded configuration. It will be appreciated that depending upon the configuration of the mating aperture 112 (FIG. 6), the mating tip 164 (FIG. 8) can have a variety of other configurations (e.g., magnets, clips, pins, etc.).

Figure 8:
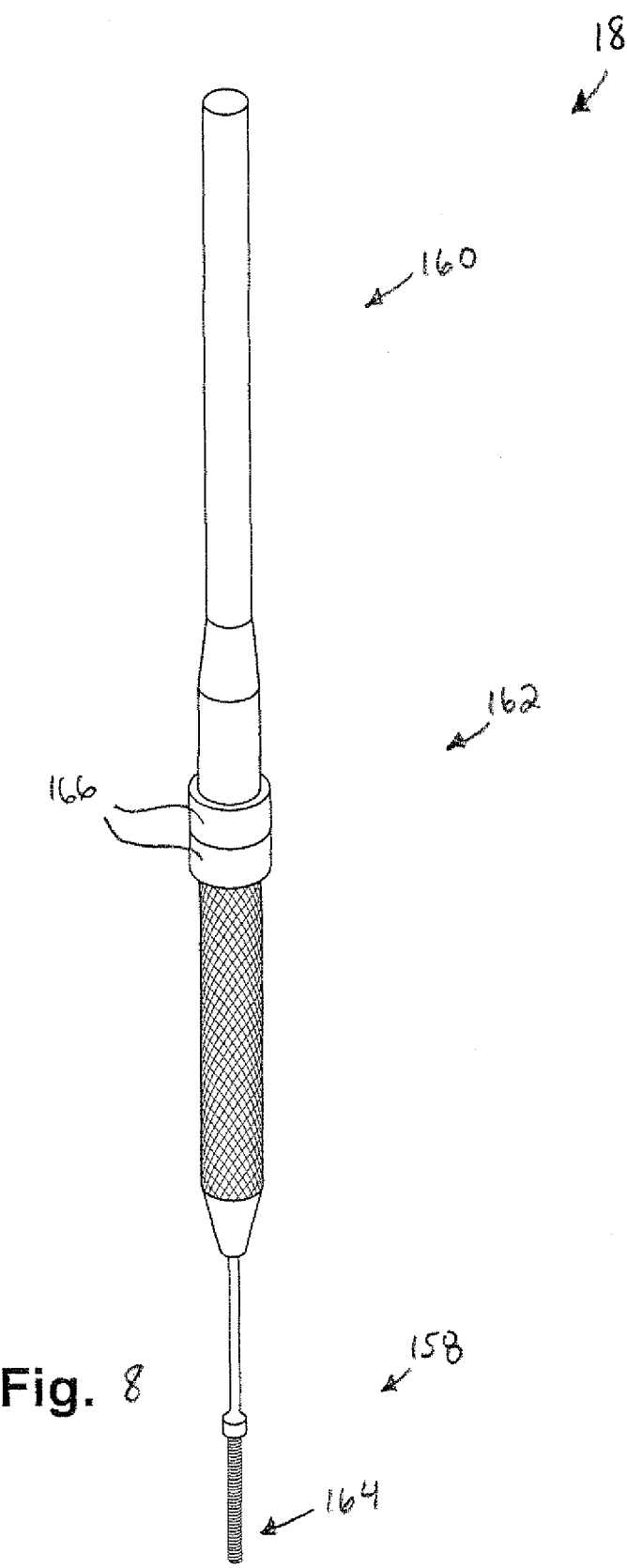
FIG. 8 is a perspective view of the removal tool in FIG. 1.

As indicated by the cross-hatched region in FIG. 8, the middle portion 162 of the removal tool 18 is textured to facilitate handling. As also shown in FIG. 8, two rubber stoppers 166 are disposed about the middle portion 162. The stoppers 166 also facilitate handling of the removal tool 18. It will be appreciated that the removal tool 18 may include a fewer or greater number of stoppers 166 than are illustrated in FIG. 8. Although the handle portion 160 is shown as having a tapered configuration, it will also be appreciated that the handle portion can have a cross-sectional area that is the same or greater than that of the middle portion 162.

In another aspect of the present invention, a system $10_a$ (FIG. 9) for vitrifying a biological specimen 12 is provided. The system $10_a$ is identically constructed as the system 10 shown in FIGS. 1-8, except where as described below. In FIGS. 9-12B, structures that are identical to structures in FIGS. 1-8 use the same reference numbers, whereas structures that are similar but not identical carry the suffix "a".

As shown in FIG. 9, the system $10_a$ comprises a vitrification apparatus $14_a$ and an applicator 16. The apparatus $14_a$ (FIGS. 10A-B) comprises a cap member 20, a plunger $22_a$, and a specimen chamber $24_a$. The plunger $22_a$ (FIGS. 11A-C) has &tubular configuration and includes an open first end portion 60, a closed second end portion $62_a$, and a channel 168 extending between the first and second end portions 60 and $62_a$. The channel 168 of the plunger $22_a$ is defined by an inner surface $66_a$ and an outer surface $68_a$. The plunger $22_a$ has a versatile construction to tolerate pressure changes and frictional forces. The plunger $22_a$ can be made of any rigid or semi-rigid material, such as a hardened plastic (e.g., polystyrene, polyethylene or polyvinylchloride), metal, or metal alloy. The plunger $22_a$ can be reusable or, alternatively, may be disposable after each use. As described in more detail below, the plunger $22_a$ is dimensioned to snugly fit inside the specimen chamber $24_a$.

The first end portion 60 of the plunger $22_a$ includes four oppositely disposed openings 70, each of which extends between the inner and outer surfaces $66_a$ and $68_a$. As shown in FIG. 11B, the second end portion $62_a$ of the plunger $22_a$ includes a ridge 170 extending circumferentially about the plunger. The ridge 170 is integrally formed with the outer surface $68_a$ of the plunger $22_a$, and includes oppositely disposed first and second surfaces 172 and 174. Each of the first and second surfaces 172 and 174 extends substantially perpendicular to the outer surface $68_a$ of the plunger $22_a$.

The outer surface $68_a$ of the second end portion $62_a$ includes at least one sealing member 78 operably secured thereon. The at least one sealing member 78 includes an O-ring made of rubber, for example. As shown in FIGS. 11A-B, separate O-rings are in contact with the first and second surfaces 172 and 174 of the ridge 170. It will be appreciated, however, that any number of sealing members 78 may be used, and that other types of sealing members, such as a removable adhesive tape (not shown) can alternatively be used. Additionally, it will be appreciated that the at least one sealing member 78 can be integrally formed with the plunger $22_a$, and that the size and shape of the at least one sealing member can be varied as needed.

As shown in FIGS. 11A-B, the plunger $22_a$ additionally comprises a filtering member 176 that extends substantially perpendicular to the channel 168 and has a disc-like shape. The filtering member 176 is formed as an integral part of the plunger $22_a$, and has a diameter that is greater than the diameter of the channel 168. It will be appreciated that the filtering member 176 can be detachable from the second end portion $62_a$ using a snap fit mechanism, for example. It will also be appreciated that the circumference of the filtering member 176 may be equal to the circumference of the outer surface $68_a$ of the plunger $22_a$.

The filtering member 176 includes a plurality of pores 178 extending between a first surface 180 and a second surface 182 (FIGS. 11B-C). The pores 178 are in fluid communication with the channel 168, and are sufficiently sized to not hinder fluid flow. Additionally, the filtering member 176 provides a backbone or support for a disposable filter 184 (FIG. 26) so that the biological specimen 12 cannot migrate through the pores 178 (FIG. 11C). It should be appreciated that the plunger $22_a$ can have pores 178 of a size sufficient to prevent migration of the biological specimen 12. In this case, there may be no need to include the disposable filter 184 (FIG. 26) as part of the plunger $22_a$ (FIGS. 11A-C). It will also be appreciated that the filtering member 176 can have any desired number of pores 178. The filtering member 176 can be made of any rigid material or semi-rigid material, such as a hardened plastic (e.g., polystyrene, polyethylene or polyvinylchloride).

Figure 12A:
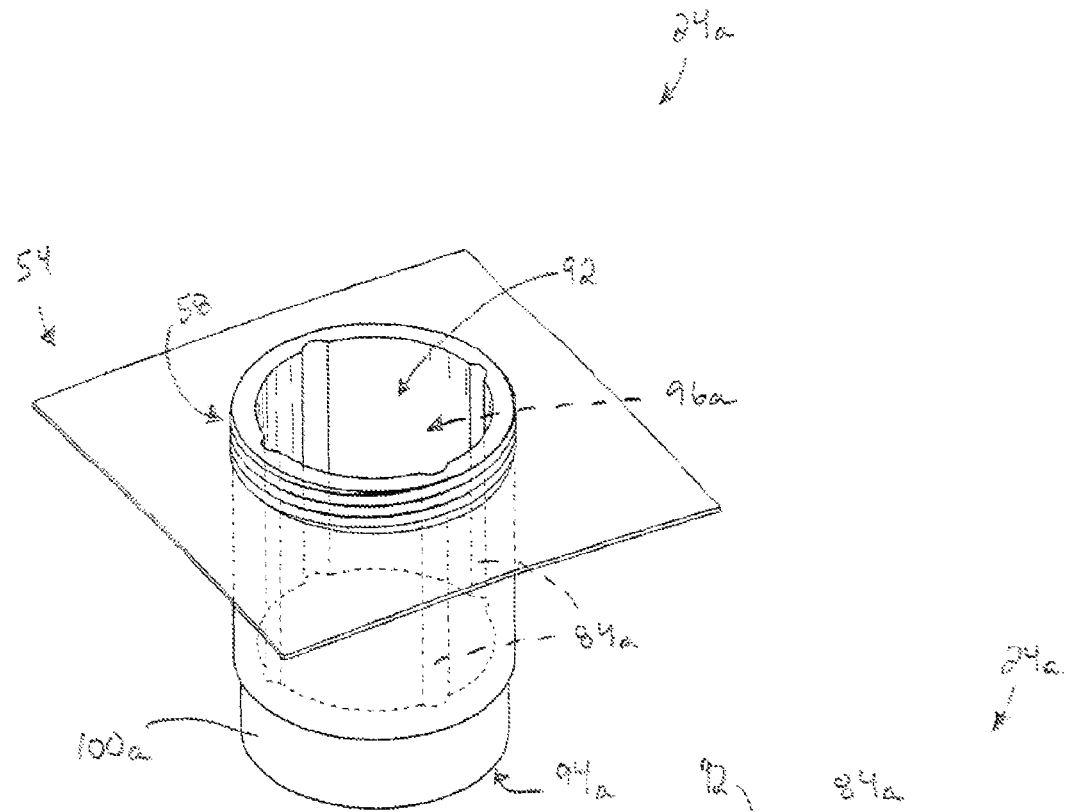
FIG. 12A is a perspective view of the specimen chamber in FIG. 10A.
Figure 12B:
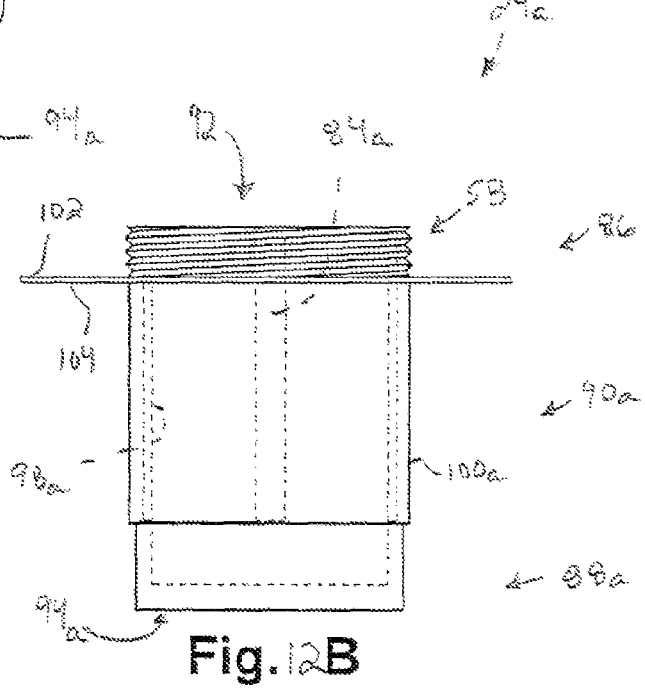
FIG. 12B is a cross-sectional view of the specimen chamber in FIG. 12A.

The specimen chamber $24_a$ (FIGS. 12A-B) has a cup-like shape for receiving the biological specimen 12 and the plunger $22_a$. As shown in FIGS. 12A-B, the specimen chamber $24_a$ comprises an open first end portion 86, a closed second end portion $88_a$, and a tapered or stepped main body portion $90_a$ extending between the first and second end portions. The first end portion 86 includes a first open end 92 and a threaded portion 58 for mating with the inner threaded portion of the cap member 20. The second end portion $88_a$ includes a second closed end $94_a$. The specimen chamber $24_a$ also includes a cavity $96_a$ (FIG. 12A) that extends between the first and second end portions 86 and $88_a$ and is defined by inner and outer surfaces $98_a$ and $100_a$.

The specimen chamber $24_a$ can be made of a rigid metallic or non-metallic material that is highly temperature conductive, such as polished aluminum, stainless steel, titanium, titanium alloy, or hardened plastic. For example, the second closed end $94_a$ of the specimen chamber $24_a$ can be made of a thin layer (or layers) of a highly temperature conductive material, such as aluminum to facilitate heat transfer between the biological specimen 12 and a cooling fluid. Although not shown in FIGS. 12A-B, it will be appreciated that the second closed end $94_a$ can have a thickness sufficient to support a plurality of axially-extending grooves to facilitate heat transfer.

The inner surface $98_a$ of the specimen chamber $24_a$ also includes at least one groove $84_a$ that extends longitudinally between the first and second end portions 86 and $88_a$. For example, the at least one groove $84_a$ can extend partly between the first open end 92 and the second closed end $94_a$ of the specimen chamber $24_a$. As shown in FIGS. 12A-B, the inner surface $98_a$ of the specimen chamber $24_a$ includes four, equally spaced apart grooves $84_a$ that extend about ¾ of the distance between the first open end 92 and the second closed end $94_a$. Although the grooves $84_a$ illustrated in FIGS. 12A-B have a linear configuration and a semi-circular cross-sectional shape, it will be appreciated that the grooves can have any desired configuration (e.g., zigzag, serpentine, etc.) and cross-sectional shape (e.g., square-like, pyramidal). The groove(s) $84_a$ facilitate insertion of the plunger $22_a$ (FIG. 10A) into the specimen chamber $24_a$ (FIGS. 12A-B) by allowing any air in the specimen chamber to travel upward through the groove(s) towards the first end portion 86 and thereby relieve pressure applied by the plunger.

The first end portion 86 of the specimen chamber $24_a$ also includes a second skirt member 54 constructed in a similar or identical manner as the first skirt member 48 (FIGS. 5A-B). The second skirt member 54 (FIGS. 12A-B) is attached along a circumferential portion of, and extends substantially radial to, the outer surface $100_a$ at the first end portion 86 of the specimen chamber $24_a$. The second skirt member 54 comprises a layer or sheet of a heat-sealable material (e.g., polyethylene) having a first surface 102 oppositely disposed from a second surface 104. The second skirt member 54 is securely attached along the circumferential portion of the outer surface $100_a$ via an adhesive or other bonding substance (not shown). Although the second skirt member 54 is shown as having a thin, square-like configuration, it will be appreciated that the second skirt member can have any desired shape (e.g., circular, rectangular) and thickness.

Figure 13:
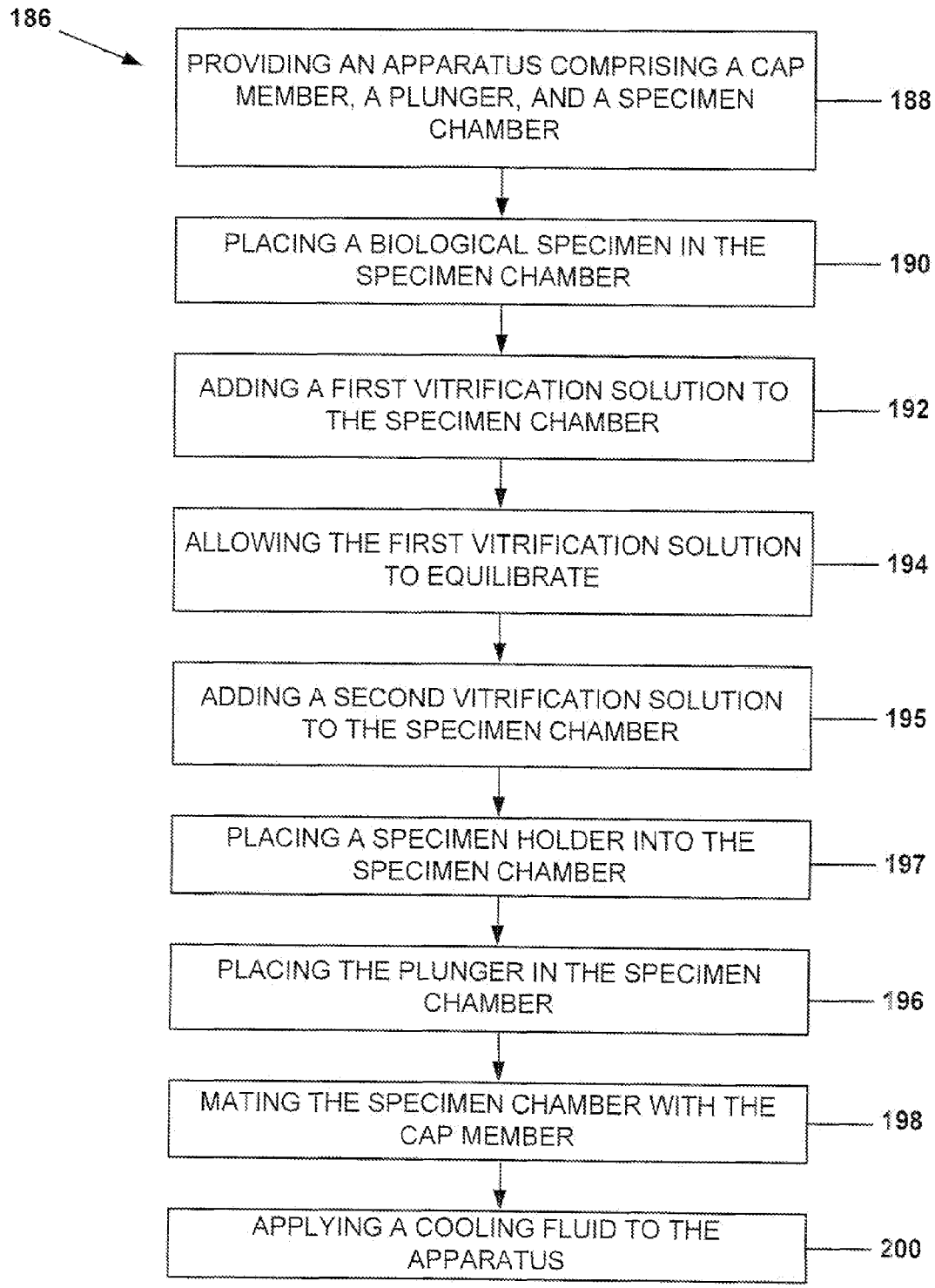
FIG. 13 is a process flow diagram illustrating a method for vitrifying a biological specimen according to another aspect of the present invention.

FIG. 13 is a process flow diagram illustrating another aspect of the present invention comprising a method 186 for vitrifying a biological specimen 12, such as a single cell type or cell suspension. It will be appreciated that the method 186 can find use in a variety of applications. For example, the method 186 may find application in medical areas, such as skin grafts, cornea storage, circulatory vessel storage, freezing of transplant tissues, infertility treatment, laboratory research (e.g., investigation of molecular regeneration diseases, such as cancer), and human-assisted reproduction, as well as animal husbandry and endangered species preservation.

As shown in FIG. 13, the method 186 includes providing an apparatus 14 comprising a cap member 20, a plunger 22, and a specimen chamber 24 at Step 188. One example of the apparatus 14 provided at Step 188 includes the apparatus illustrated in FIGS. 2A-B, which additionally includes a specimen holder 106. Either prior to, contemporaneous with, or after providing the apparatus 14, a biological specimen 12 (e.g., a single cell type or cell suspension) is prepared. To prepare the biological specimen 12, one or more specimens are collected from a subject by any appropriate means known in the art.

At Step 190, the biological specimen 12 (e.g., a single cell type or cell suspension) is placed at the bottom of the specimen chamber 24. After placing the biological specimen 12 into the specimen chamber 24, a first vitrification solution is contacted with the biological specimen at Step 192. The first vitrification solution comprises a base medium and a cryoprotectant. For example, about 2 ml of the first vitrification solution can be added to the specimen chamber 24 after placing the biological specimen 12 in the specimen chamber. It will be appreciated that a desired volume of the first vitrification solution can be added to the specimen chamber 24 either before, during, or after the biological specimen 12 is placed in the specimen chamber.

The base medium can be any type of solution that maintains cellular integrity under in vitro conditions, such as a physiological buffer maintained at a desired temperature. Depending on the type of tissue comprising the biological specimen 12 (e.g., a single cell type or cell suspension), any one or combination of cryoprotectants can be added to the base medium. Cryoprotectants can include, but are not limited to, formamide, 1,2-propanediol, 2,3-butanediol, glycerol, ethylene glycol, n-dimethyl formamide, 1,3-propanediol, polyethylene glycol, dimethylsulfoxide (DMSO), sugars, and methylpentanediol, as well as others known in the art.

The method 186 also allows for the use of one or more impermeable cryoprotectant agents, such as polyvinylpyrrolidone or hydroxyethyl starch that may be more effective at protecting biological specimens 12 (e.g., a single cell type or cell suspension) cooled at rapid rates. Such agents are often large macromolecules, which affect the properties of the cryoprotectant solution to a greater extent than would be expected from their osmotic pressure. Some of these non-permeating cryoprotectant agents have direct protective effects on the cell membrane. When such cryoprotectants are used in extremely high concentrations, ice formation may be eliminated entirely during cooling to (and warming from) cryogenic temperatures. Impermeable cryoprotectants can include, without limitation, agarose, dextrans, glucose, hydroxyethylstarch, inositol, lactose, methyl glucose, polyvinylpyrrolidone, sorbitol, sucrose and urea.

After contacting the biological specimen 12 (e.g., a single cell type or cell suspension) with the first vitrification solution, the specimen is allowed to equilibrate for a desired period of time (e.g., about 15 minutes) at Step 194. Next, a second vitrification solution is slowly contacted with the biological specimen 12 (e.g., a single cell type or cell suspension) at Step 195 by adding a desired volume of the second vitrification solution into the specimen chamber 24. The second vitrification solution comprises a base medium and at least one cryoprotectant. The second vitrification solution can have a similar or identical composition as the first vitrification solution, except that the concentration of the cryoprotectant in the second vitrification is greater than the concentration of the cryoprotectant in the first vitrification solution. The second vitrification solution is contacted with the first vitrification solution until a final volume having a desired concentration of cryoprotectant(s) (e.g., about 30% to about 50%) is achieved.

Once a desired volume of the first and second vitrification solutions has been added to the specimen chamber 24, the specimen holder 106 is placed into the specimen chamber over the biological specimen 12 (e.g., a single cell type or cell suspension) at Step 197. The specimen holder 106 can be placed by hand into the specimen chamber 24 (e.g., using forceps or tweezers) or, alternatively, by mating the removal tool 18 with the specimen holder and then gently placing the specimen holder in the specimen chamber. Placement of the specimen holder 106 over the biological specimen 12 displaces the cells into the pores 108 of the specimen holder (FIGS. 15-16), which facilitates heat transfer between the specimen and the cooling fluid.

Figure 14:
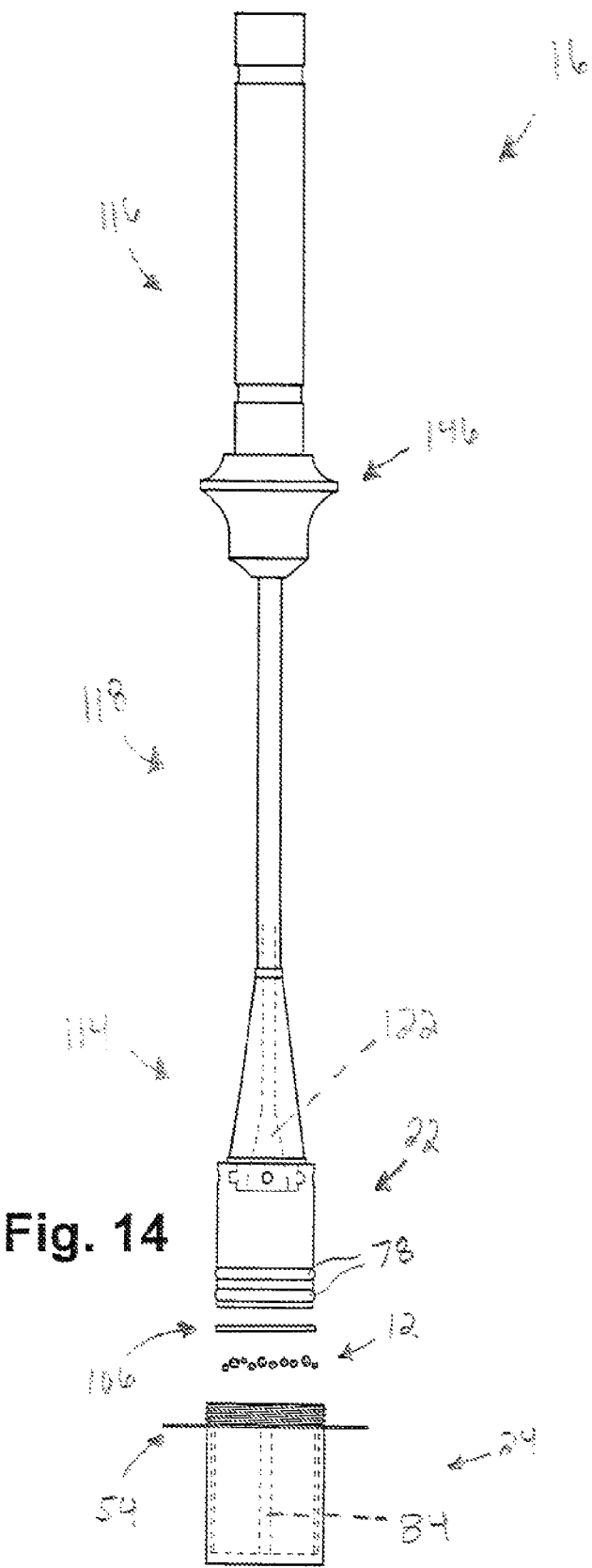
FIG. 14 is a cross-sectional view showing the applicator in FIG. 1 mated with the plunger and being positioned atop the specimen, the specimen holder, and the specimen chamber.

At Step 196, the plunger 22 (FIG. 14) is inserted into the specimen chamber 24 using the applicator 16. Prior to inserting the plunger 22, the plunger is mated with the 114 mating portion of the applicator 16. To mate the plunger 22 and the mating portion 114, an axial force is applied (e.g., using tactile means) at the first end 148 of the abutment member 146 so that the abutment member slides over the first end 152 of the handle portion 116. As the radial force is applied to the abutment member 146, the actuating mechanism causes the actuator member 122 to partially extend from the casing 120. Partial movement of the actuator member 122 out of the casing 120 relieves tension on the pins 134, in turn causing the pins to partially retract into the casing.

Figure 15:
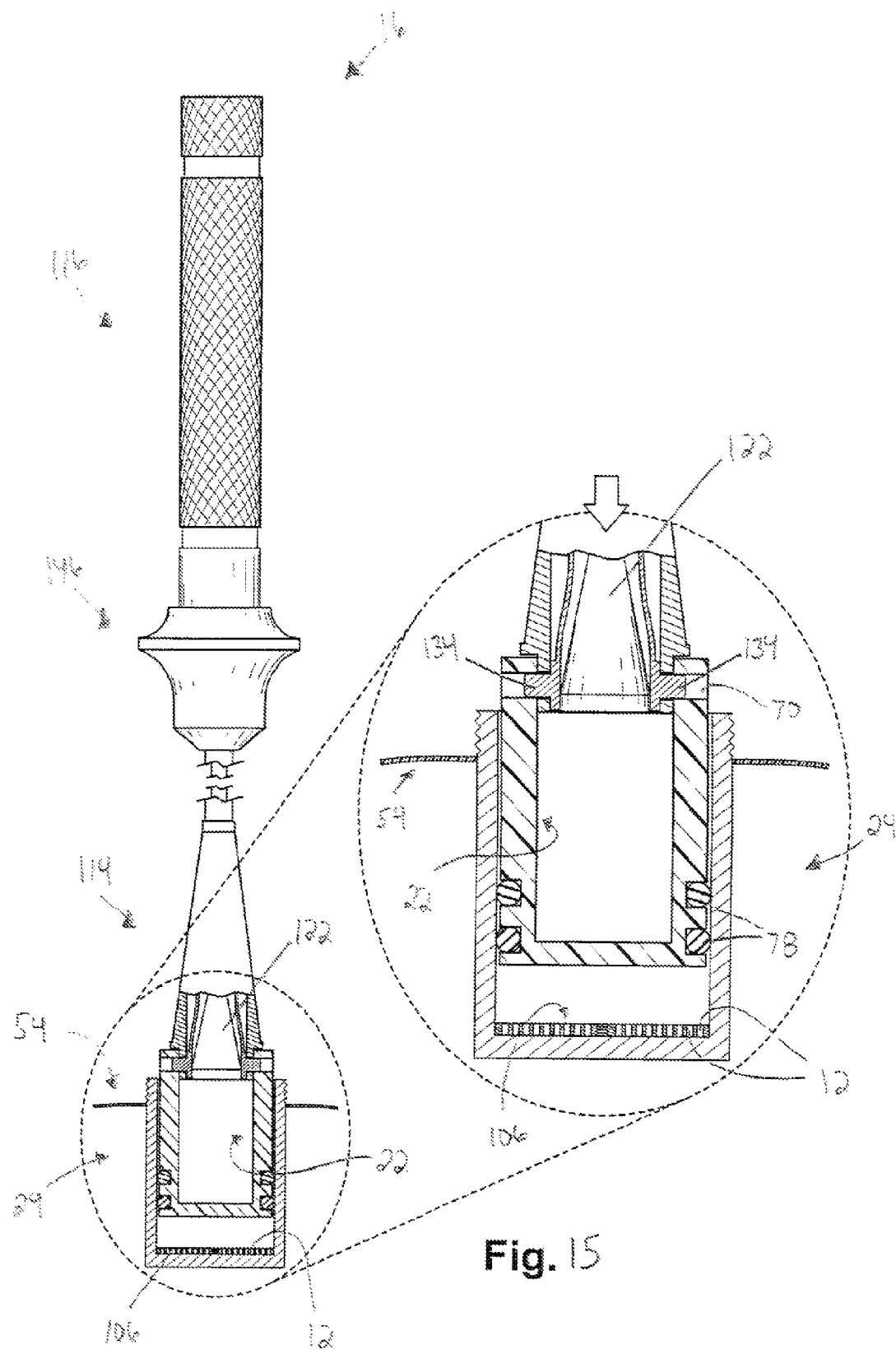
FIG. 15 is a cross-sectional view similar to FIG. 7B but showing the applicator mated with the plunger, which is being disposed in the specimen chamber.

Once the pins 134 are fully retracted into the casing 120, the first end portion 124 of the casing is mated with the first end portion 60 of the plunger 22. Next, the abutment member 146 is released, thereby causing the actuator member 122 to at least partially withdraw into the casing 120. As the actuator member 122 is withdrawn into the casing 120, the actuator member displaces the pins 134 outward into contact with the respective openings 70 of the plunger 22. With the applicator 16 now securely mated with the plunger 22, the plunger is inserted into the specimen chamber 24 as shown in FIG. 15.

Figure 16:
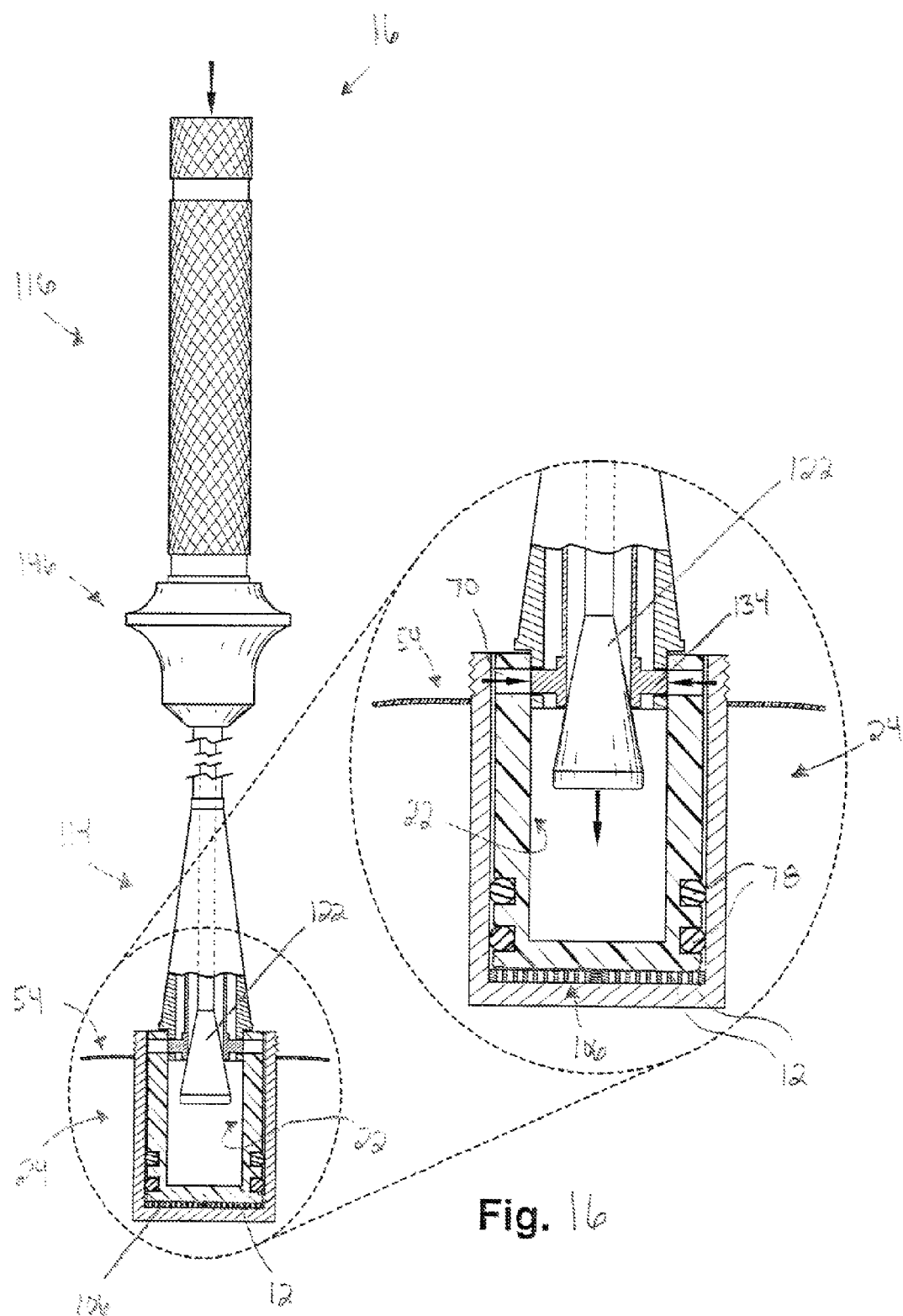
FIG. 16 is an exploded cross-sectional view showing the plunger fully inserted into the specimen chamber.

Insertion of the plunger 22 into the specimen chamber 24 causes any air to pass upward through the longitudinal grooves 84 of the specimen chamber, thereby relieving pressure as the applicator 16 is pressed downward. A suction device (not shown) (e.g., a pipette) can be used to remove any excess of the first vitrification solution from the specimen chamber 24. As shown in FIG. 16, the applicator 16 is then detached from the plunger 22 by once again applying a radial force at the first end 148 of the abutment member 146 so that the pins 134 are retracted from the openings 70 of the plunger and the plunger remains in the specimen chamber 24. The plunger 22 is kept in place to allow slight pressure on the biological specimen 12, keeping the specimen in direct contact with a minimal volume of vitrification solution surrounding the specimen.

Figure 20:
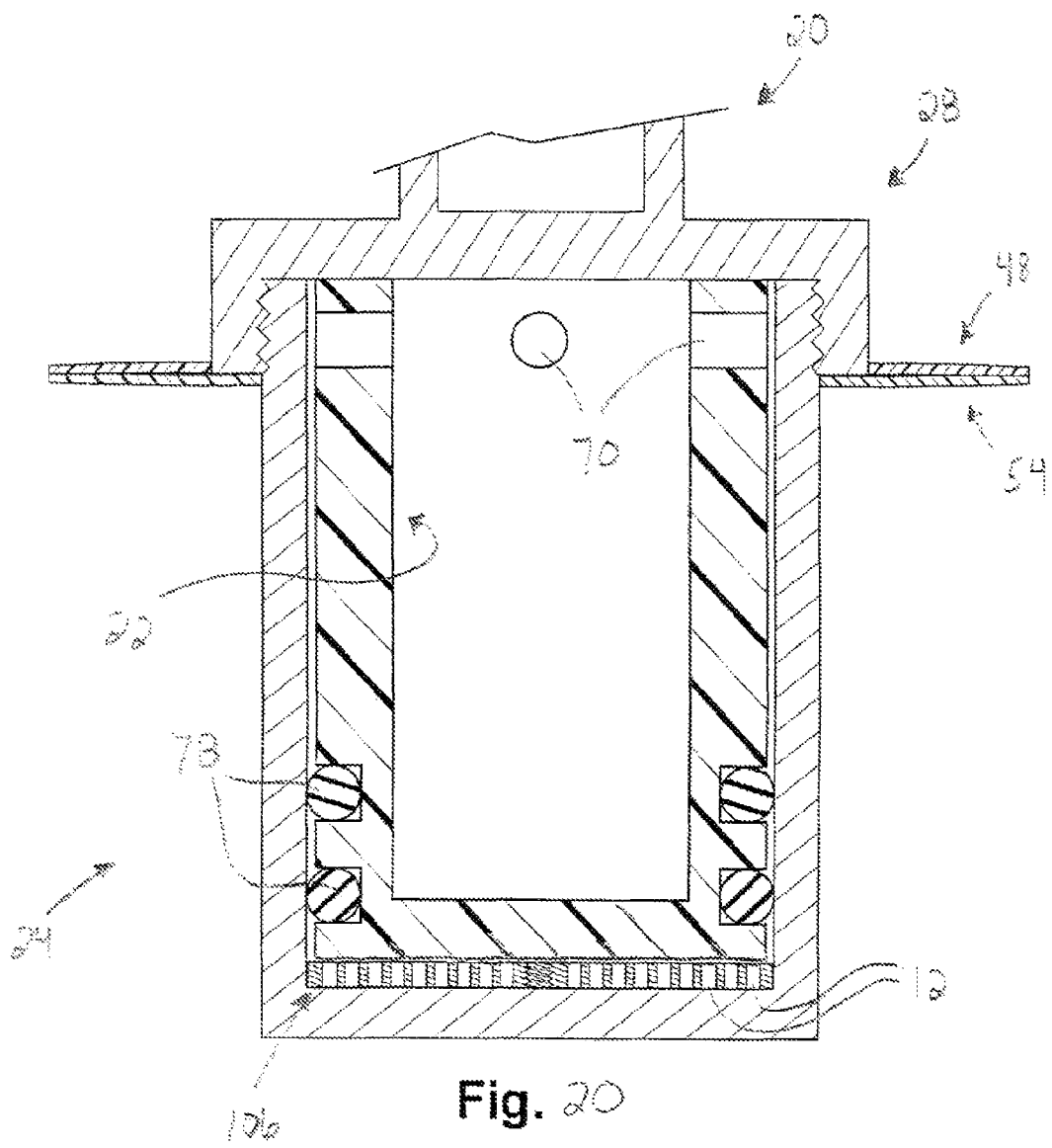
FIG. 20 is an exploded cross-sectional view of the apparatus in FIG. 16.

As shown in FIG. 17, the specimen chamber 24 is then mated with the cap member 20 at Step 198. More particularly, the threaded portion 58 of the specimen chamber 24 is mated with the inner threaded portion of the recess 56 by screwing the specimen chamber into the receiving portion 28. As the specimen chamber 24 is screwed into the cap member 20, a portion of the second surface 52 of the first skirt member 48 and a portion of the first surface 102 of the second skirt member 54 are pressed into contact with one another. With the cap member 20 and the specimen chamber 24 securely mated to one another, heat (indicated by $\Delta$ in FIG. 18) is applied to the first and second skirt members 48 and 54 using an appropriate heat source (not shown). Heat is applied for a time and at a temperature sufficient to bond or seal the first and second skirt members 48 and 54 together (FIGS. 19-20). The seal created between the first and second skirt members 48 and 54 prevents cooling fluid from entering the specimen chamber 24.

After the first and second skirt members 48 and 54 are sealed together, a holding device (not shown) is mated with the stem portion 26 of the cap member 20. At Step 200, a cooling fluid (e.g., liquid nitrogen) is then applied to the apparatus 14 by, for example, dunking the apparatus into a vessel (not shown) containing the cooling fluid for an amount of time (e.g., about 20 seconds) sufficient to cryogenically preserve the biological specimen 12 (e.g., a single cell type or cell suspension). When placed in the cooling fluid, the apparatus 14 can be swirled to promote contact of the apparatus with the cooling fluid and thereby facilitate rapid freezing of the biological specimen 12. Swirling the apparatus 14 in the cooling fluid also prevents or reduces gas bubble formation around the apparatus during the cooling process, which can increase the heat transfer rate.

Figure 21:
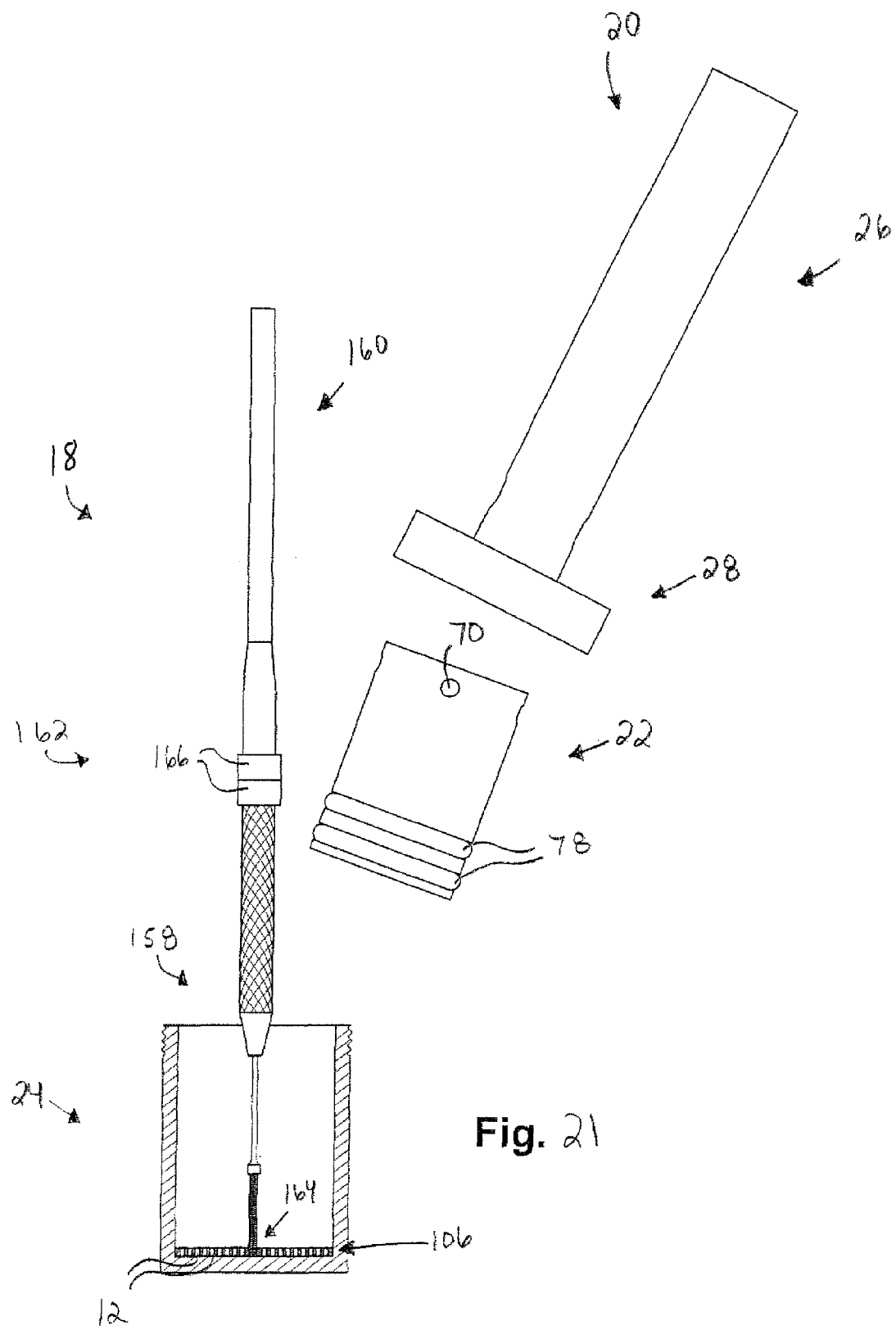
FIG. 21 is a cross-sectional view showing the apparatus in FIG. 16 being disassembled and the removal tool mated with the specimen holder.

When the vitrified biological specimen 12 (e.g., a single cell type or cell suspension) is ready for use, the specimen can be rapidly thawed so that little or no damage to viability, structure, and/or function of the specimen results. To thaw the biological specimen 12, the apparatus 14 is removed from cryostorage (e.g., from liquid nitrogen) and placed into a warm water bath (not shown) to facilitate rapid thawing. After an appropriate period of time (e.g., about 15 seconds), the apparatus 14 is removed from the water bath, dried, and the cap member 20 removed from the specimen chamber 24 (FIG. 21).

Prior to removing the cap member 20, a cutting instrument (not shown) (e.g., a knife or scissors) is used to break the seal formed by the first and second skirt members 48 and 54. After removing the cap member 20, the mating portion 114 of the applicator 16 is then mated with the first end portion 60 of the plunger 22 (as described above) and withdrawn to remove the plunger from the specimen chamber 24. Once the plunger 22 is withdrawn from the specimen chamber 24, about 2 ml of a thawing solution is added to the specimen chamber. The thawing solution can comprise a $CO_2$-independent media containing about 20% serum substitute supplement, about 35 μg/ml gentamicin, and about 1 M sucrose.

After about 1 minute, the plunger 22 is placed back into the specimen chamber 24 (using the applicator 16, as described above), and any excess thawing solution is removed from the specimen chamber. The plunger 22 is again removed from the specimen chamber 24, and about 2 ml of a dilution solution is then added to the specimen chamber. The dilution solution can comprise a $CO_2$-independent media containing about 20% serum substitute supplement, about 35 μg/ml gentamicin, and about 0.5 M sucrose. After about 5 minutes, the plunger 22 is placed inside the specimen chamber 24 and any excess dilution solution is removed from the specimen chamber.

Figure 22:
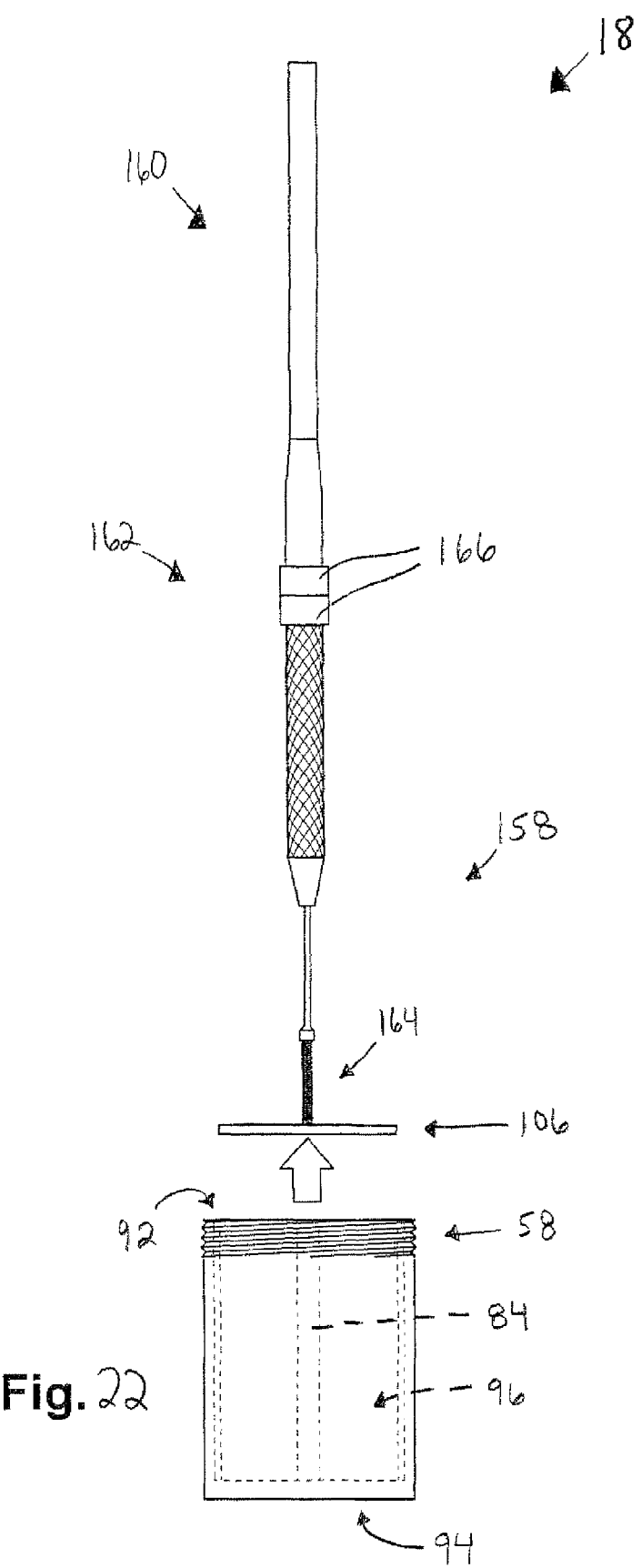
FIG. 22 is a cross-sectional view showing the removal tool in FIG. 21 being withdrawn from the specimen chamber.

Next, the plunger 22 is removed from the specimen chamber 24 and about 2 ml of a washing solution is added to the specimen chamber. The washing solution can comprise a $CO_2$-independent media containing about 20% serum substitute supplement and about 35 μg/ml gentamicin. After about 10 minutes, the mating tip 164 of the removal tool 18 can be mated (e.g., threaded) with the mating aperture 112 of the specimen holder 106 (FIG. 21). As shown in FIG. 22, the removal tool 18 can then be withdrawn from the specimen chamber 24 so that the specimen holder 106, along with the thawed biological specimen 12 (e.g., a single cell type or cell suspension), is removed. Depending upon the type of biological specimen 12, the specimen can then be placed in a nutritive solution (e.g., a culture or transplant media) for any desired use.

Figure 23:
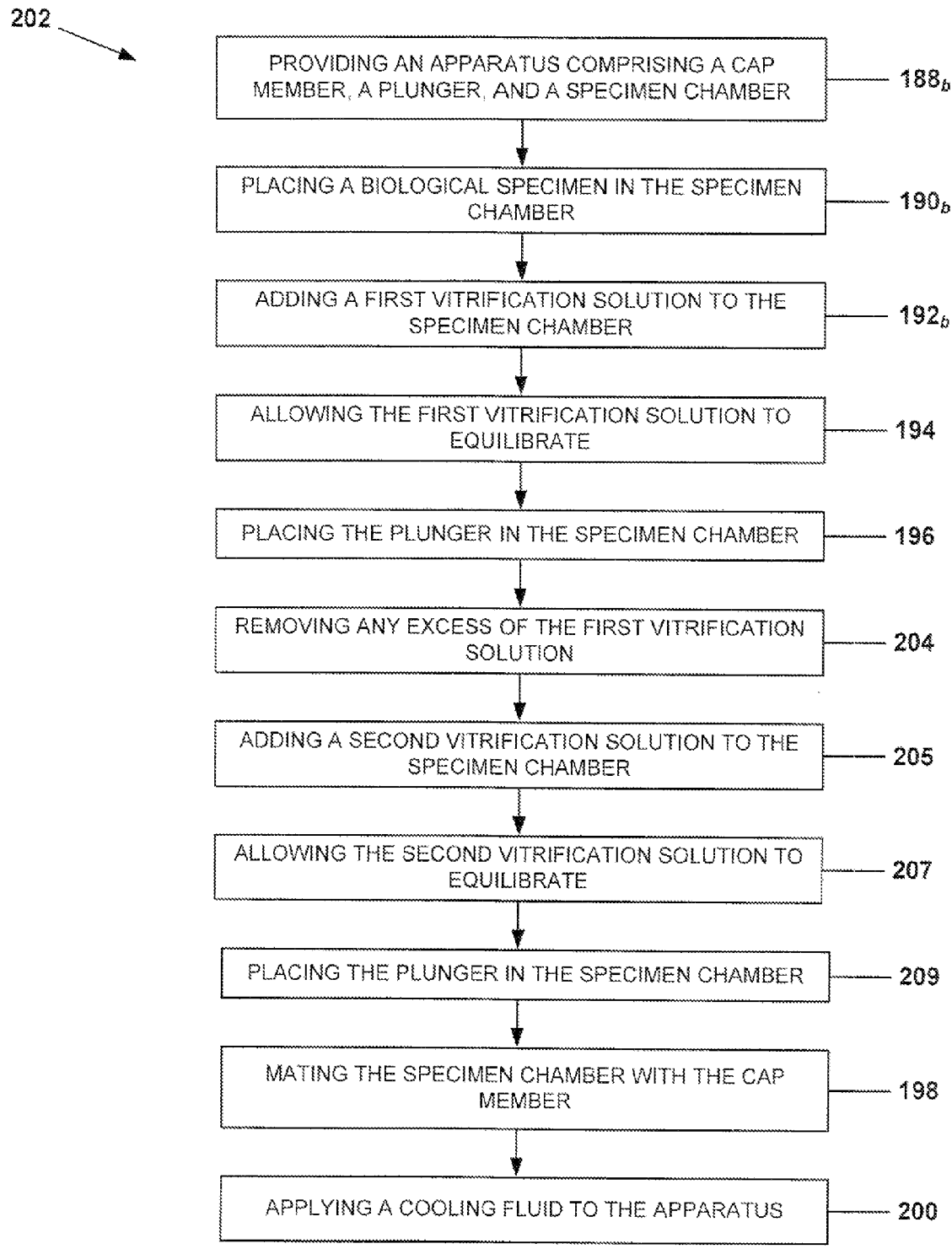
FIG. 23 is a process flow diagram illustrating a method for vitrifying a biological specimen according to another aspect of the present invention.

In another aspect of the present invention, a method 202 (FIG. 23) for vitrifying a biological specimen 12 (e.g., a tissue slice or tissue fragment) is provided. The steps of the method 202 are identical to the steps of the method 186 shown in FIG. 13, except where as described below. In FIG. 23, steps that are identical to steps in FIG. 13 use the same reference numbers, whereas steps that are similar but not identical carry the suffix "b".

Although the method 202 will be described in terms of vitrifying a tissue slice or tissue fragment 12 (e.g., an ovarian tissue fragment), it will be appreciated that the method can find use in a variety of applications including, but not limited to, medical areas, such as skin grafts, cornea storage, circulatory vessel storage, freezing of transplant tissues, infertility treatment, laboratory research (e.g., investigation of molecular regeneration diseases, such as cancer), and human-assisted reproduction, as well as animal husbandry and endangered species preservation.

As shown in FIG. 23, the method 202 includes providing an apparatus $14_a$ at Step $188_b$. One example of the apparatus $14_a$ provided at Step $188_b$ includes the apparatus illustrated in FIGS. 10A-B. Either prior to, contemporaneous with, or after providing the apparatus $14_a$, a biological specimen 12 (e.g., a tissue slice or tissue fragment) is then prepared. To prepare the biological specimen 12, one or more specimens are collected from a subject by any appropriate means known in the art. For example, in a female human subject about to undergo chemotherapy or radiotherapy, one or more ovarian follicles can be harvested for cryopreservation. To do so, the cortex of the ovary can be sliced into slices having a thickness of about 0.5 mm after removal of the medulla of ovary (also known as the Zona vasculosa of Waldeyer). Using a tissue chopper (not shown) having a desired slice setting (e.g., so the slices are automatically cut at about 500 μm intervals in 2 perpendicular planes), the previously prepared slices can be minced or chopped into smaller fragments having a volume of between about 0.5 mm$^3$ and about 1 mm$^3$.

If it has not been done so already, the plunger $22_a$ is prepared for use with a sealing member applicator 206 as shown in FIGS. 24-26. The sealing member applicator 206 has an elongated, cup-like configuration and includes a proximal end portion 208, a distal end portion 210, and a main body portion 212 extending between the end portions. The proximal end portion 208 includes an opening 214 that extends between the proximal end portion and the distal end portion 210, and is defined by an inner surface 216 and an outer surface 218. As shown in FIGS. 24-26, the sealing member applicator 206 also includes a shelf 220 that extends circumferentially around the outer surface 218. The sealing member applicator 206 can be made of any rigid or semi-rigid material, such as a metal (e.g., aluminum) or hardened plastic (e.g., polyvinyl chloride).

To prepare the plunger $22_a$, a sealing member 78 (e.g., an O-ring) is placed about the outer surface 218 at the proximal end portion 208 of the sealing member applicator 206. Next, a disposable filter 184 is placed atop the proximal end portion 208 as shown in FIG. 26. The disposable filter 184 has a flattened, disc-like configuration and includes a plurality of pores 222 extending between first and second surfaces 224 and 226. The pores 222 can have any desired diameter; however, the pores should be sufficiently sized so that the biological specimen 12 (e.g., a tissue slice or tissue fragment) does not flow through the pores and into the channel 168 of the plunger $22_a$. Additionally, the diameter of the disposable filter 184 should be greater than the diameter of the plunger $22_a$. One example of a disposable filter 184 that may be used with the present invention can include a 100 μm nylon net filter.

The disposable filter 184 can be discarded after each use of the apparatus $14_a$ or, alternatively, used repeatedly as desired. Where removal of the disposable filter 184 is desired following vitrification, for example, the sealing member 78 can be slid off of the second end portion $62_a$ of the plunger $22_a$ using tactile force. Then, a pair of forceps (not shown) or other similar device can be used to remove the disposable filter 184 from the plunger $22_a$. A new disposable filter (not shown) can replace the discarded disposable filter 184 as described above.

Figures 27, 28:
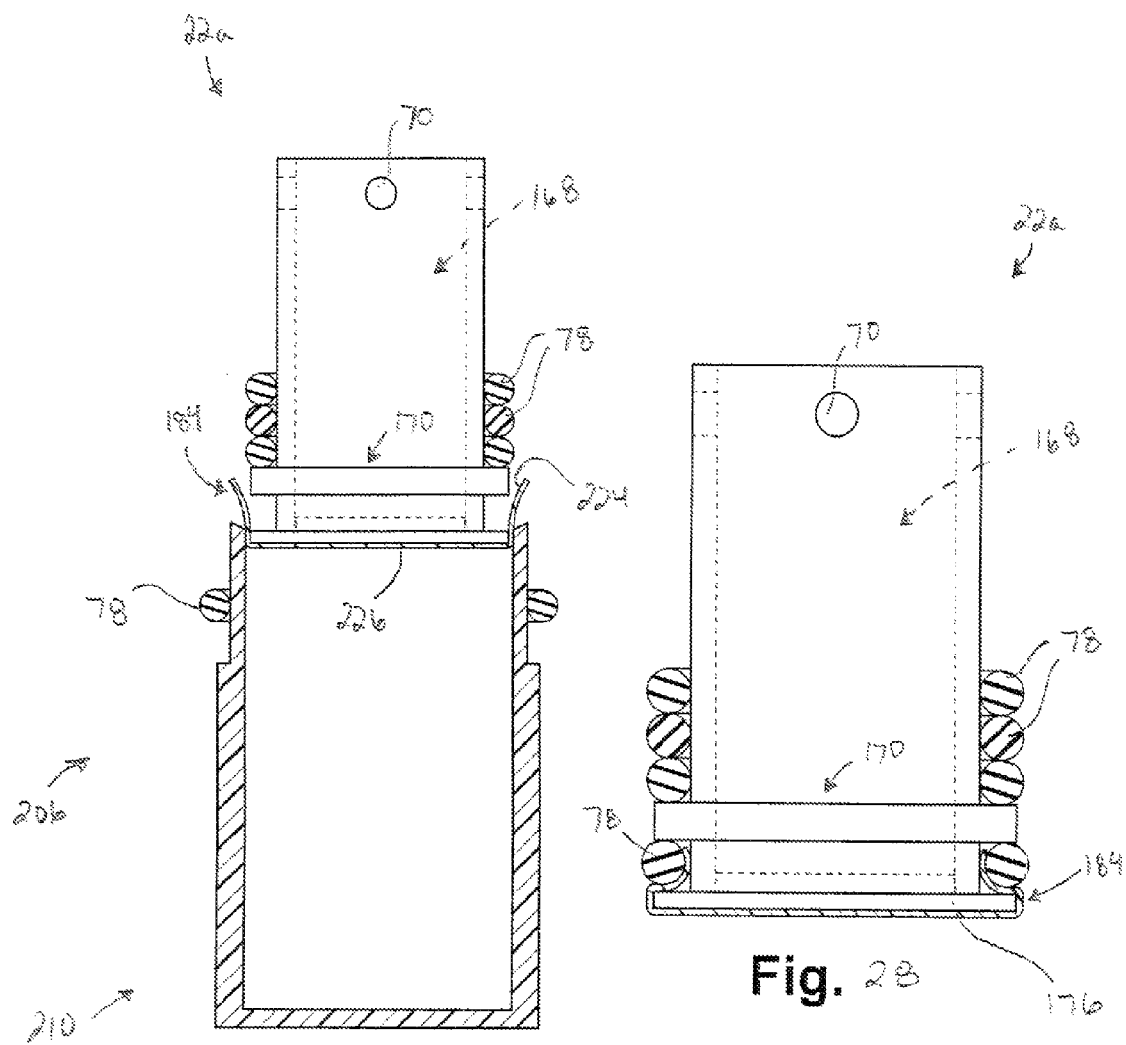
FIG. 27 is a cross-sectional view showing the sealing member applicator in FIG. 26 being used to apply the disposable filter and a sealing member to the plunger.
FIG. 28 is a cross-sectional view showing the plunger in FIG. 27 with the sealing member and the disposable filter affixed thereto.

As shown in FIG. 27, the sealing member applicator 206 is then mated (indicated by arrows) with the plunger $22_a$ so that the first surface 224 of the disposable filter 184 contacts the second surface 182 of the filtering member 176. Upon mating the plunger $22_a$ with the sealing member applicator 206, tactile force is used to slide the sealing member 78 over the proximal end portion 208 of the sealing member applicator into contact with the disposable filter 184. As the sealing member 78 is rolled over the disposable filter 184, the outer edge (not shown in detail) of the disposable filter becomes sandwiched between the sealing member 78 and the plunger $22_a$ (FIG. 28). More particularly, the first surface 224 of the disposable filter 184 is pressed against the outer surface $68_a$ of the plunger $22_a$ located between the ridge 170 and the filtering member 176.

After preparing the plunger $22_a$ and the biological specimen 12 (e.g., a tissue slice or tissue fragment), the specimen may be in one or multiple pieces, and may be pre-processed in a solid or semi-solid disc-like shape. The biological specimen 12 is then transferred into the specimen chamber $24_a$ at Step $190_b$ where it is contacted with a first vitrification solution comprising a base medium and a cryoprotectant. It will be appreciated that a desired volume of the first vitrification solution can be added to the specimen chamber $24_a$ at Step $192_b$ either before, during, or after the biological specimen 12 is placed in the specimen chamber. For example, about 2 ml of the first vitrification solution can be added to the specimen chamber $24_a$ after placing an ovarian tissue sample in the specimen chamber.

Examples of base media and cryoprotectants that can be used to form the first vitrification solution are described above. Where cryopreservation of ovarian tissue is desired, for example, the first vitrification solution can comprise a $CO_2$-independent media containing about 7.5% DMSO, about 7.5% ethylene glycol, about 20% serum substitute supplement, and about 35 µg/ml gentamicin.

Examples of impermeable cryoprotectant agents that may additionally or optionally be used with the method are also described above.

Figure 29:
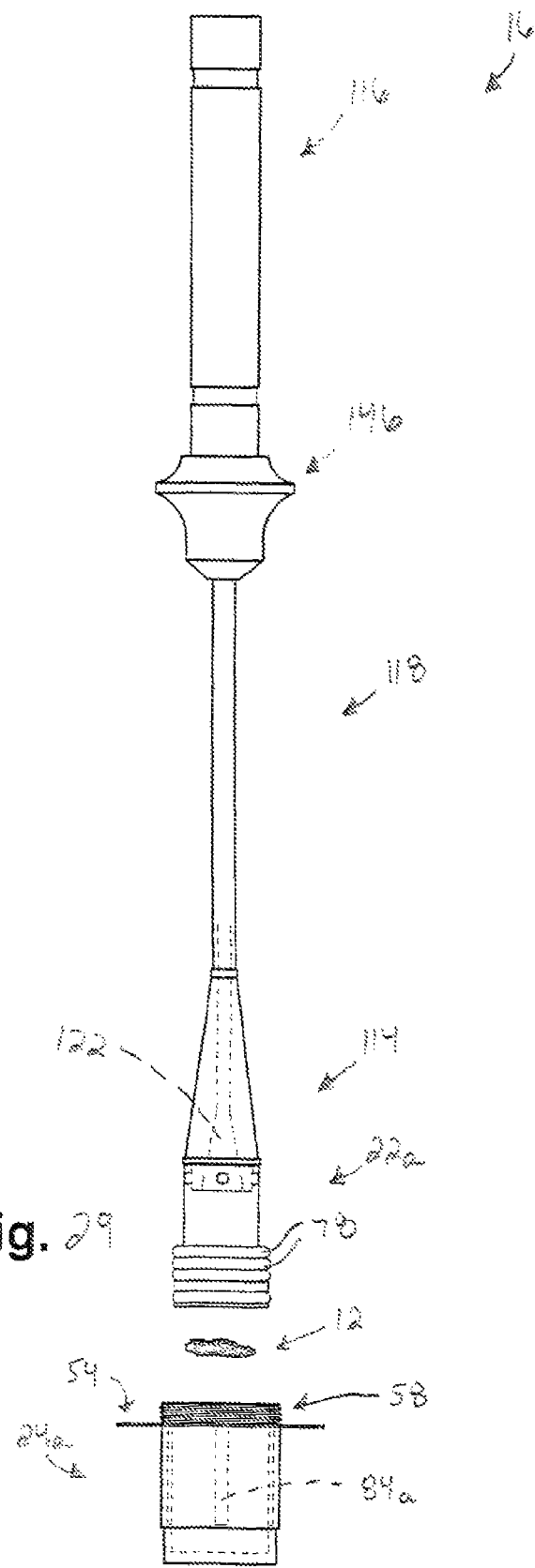
FIG. 29 is a cross-sectional view showing the applicator in FIG. 9 mated with the plunger and being positioned atop the specimen and the specimen chamber.
Figure 30:
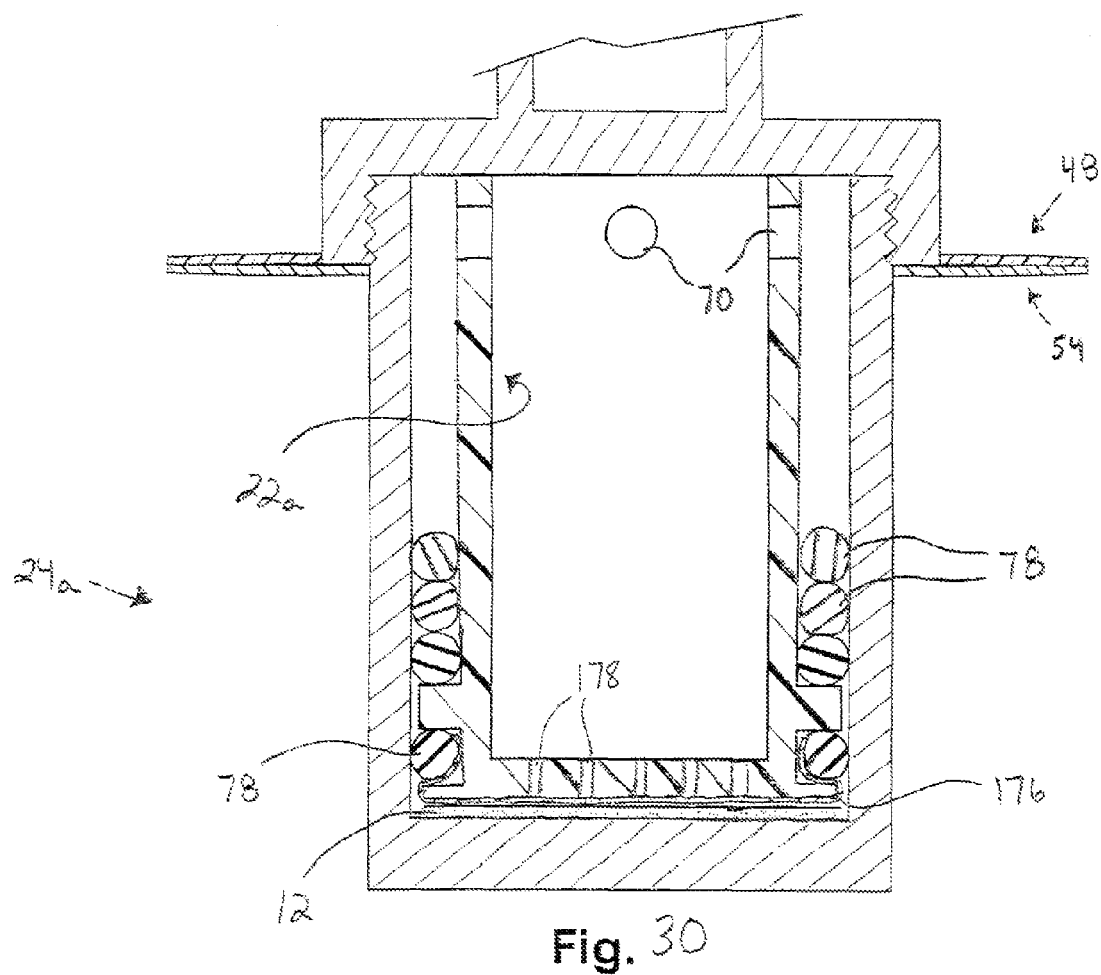
FIG. 30 is an exploded cross-sectional view showing the plunger of FIG. 29 inserted in the specimen chamber.

After contacting the biological specimen 12 (e.g., a tissue slice or tissue fragment) with the first vitrification solution, the specimen is then allowed to equilibrate for a desired period of time (e.g., about 15 minutes) at Step 194. Following equilibration of the biological specimen 12, the plunger $22_a$ is inserted into the specimen chamber $24_a$ at Step 196 using the applicator 16 (as described above). With the applicator 16 now securely mated with the plunger $22_a$, the plunger is inserted into the specimen chamber $24_a$ as shown in FIGS. 29-30.

Placement of the plunger $22_a$ in the specimen chamber $24_a$ causes any excess of the first vitrification solution to pass upward through the through the pores 222 of the disposable filter 184 and the pores 178 of the filtering member 176 into the channel 168 of the plunger. A suction device (not shown) (e.g., a pipette) is then used to remove any excess of the first vitrification solution from the channel 168 at Step 204. Next, the plunger $22_a$ is removed from the specimen chamber $24_a$ (e.g., by pulling the applicator 16), as described above.

A second vitrification solution is contacted with the biological specimen 12 (e.g., a tissue slice or tissue fragment) at Step 205 by adding a desired volume of the second vitrification (described above) solution into the specimen chamber $24_a$. To cryopreserve an ovarian tissue sample, for example, the second vitrification solution can comprise a $CO_2$-independent media containing about 15% DMSO, about 15% ethylene glycol, about 20% serum substitute supplement, about 35 µg/ml gentamicin, and about 0.5 M sucrose. The second vitrification solution is then allowed to equilibrate at Step 207.

After contacting the biological specimen 12 (e.g., a tissue slice or tissue fragment) with the second vitrification solution, the same procedure for applying and removing the vitrification solutions through the channel 168 is repeated (as described above). At Step 209, for example, the plunger $22_a$ is re-inserted into the specimen chamber $24_a$. The plunger $22_a$ is kept in place to allow slight pressure on the biological specimen 12, keeping the specimen in direct contact with the bottom of the specimen chamber $24_a$ with a minimal volume of solution surrounding the specimen.

Next, the first end portion 86 of the specimen chamber $24_a$ is mated with the receiving portion 28 of the cap member 20 at Step 198 (as described above). With the cap member 20 and the specimen chamber $24_a$ securely mated to one another, heat is applied to the first and second skirt members 48 and 54 for a time and at a temperature sufficient to bond or seal the first and second skirt members together (as described above). After the first and second skirt members 48 and 54 are sealed together, a holding device (not shown) is mated with the stem portion 26 of the cap member 20.

At Step 200, a cooling fluid (e.g., liquid nitrogen) is then applied to the apparatus $14_a$ by, for example, dunking the apparatus into a vessel (not shown) containing the cooling fluid for an amount of time (e.g., about 20 seconds) sufficient to cryogenically preserve the biological specimen 12 (e.g., a tissue slice or tissue fragment). When placed in the cooling fluid, the apparatus $14_a$ can be swirled to promote contact of the apparatus with the cooling fluid and thereby facilitate rapid freezing of the biological specimen 12. Swirling the apparatus $14_a$ in the cooling fluid also prevents or reduces gas bubble formation around the apparatus during the cooling process, which can increase the heat transfer rate.

When the vitrified biological specimen 12 (e.g., a tissue slice or tissue fragment) is ready for use, the specimen can be rapidly thawed so that little or no damage to viability, structure, and/or function of the specimen results. To thaw the biological specimen 12, the apparatus $14_a$ is removed from cryostorage (e.g., from liquid nitrogen). Next, the apparatus $14_a$ is placed into a warm water bath (not shown) to facilitate rapid thawing. To thaw a vitrified sample of ovarian tissue, for example, the apparatus $14_a$ is removed from the cooling fluid and then immediately placed in a water bath at about 39° C. A detailed description of the steps used to thaw the biological specimen 12 is provided above.

The methods 186 and 202 of the present invention presents several advantages over prior art methods used to vitrify biological tissues including, but not limited to: (1) efficient handling of biological tissue specimens 12 by the apparatus 14 and $14_a$ allows exposure time of specimens with vitrification and/or thawing solutions to be executed precisely as designated in a protocol, and to be delivered evenly to all the specimen being vitrified; (2) little or no delay in heat transfer through thick biological specimens; (3) contact of biological specimens with the specimen holder 106 promotes maximal heat propagation; (4) homogeneity of biological specimens allows only a minimal volume of vitrification solution(s) to surround specimens during vitrification; and (5) rapid removal and replacement of media (e.g., vitrification solution, thawing solution, etc.) during vitrification and thawing provides more precise control over the vitrification and thawing processes.

From the above description of the invention, those skilled in the art will perceive improvements, changes and modifications. For example, it will be appreciated that the apparatus 14 and $14_a$ can be sterilized using an autoclave prior to use. Additionally, it will be appreciated that the methods 186 and 202 can include contacting a biological specimen 12 with other types of solutions, such as physiological buffers either prior to, contemporaneous with, or after contact with the first and/or second vitrification solutions. Further, it will be appreciated that the method 186 may not include the use of the specimen holder 106. Such improvements, changes, and modifications are within the skill of the art and are intended to be covered by the appended claims.

Having described the invention, we claim:

1. A system for vitrifying a biological specimen, said system comprising:
   an apparatus comprising:
      a cap member including a stem portion integrally formed with a receiving portion, said receiving portion having a disc-like shape and including an outer surface, said outer surface including a first skirt member comprised of a heat-sealable material, said first skirt member being attached along a circumferential portion of said outer surface;

a tubular plunger having an open first end portion and a closed second end portion; and a specimen chamber for receiving said plunger, said specimen chamber having an open first end portion, a closed second end portion, and a cavity extending between said first and second end portions, said cavity being defined by oppositely disposed inner and outer surfaces, said specimen chamber further including a second skirt member comprised of heat-sealable material, said second skirt member being attached along a circumferential portion of said outer surface; and an applicator for inserting and withdrawing said plunger from said specimen chamber, said applicator comprising a mating portion, a handle portion, and a main body portion extending between said mating portion and said handle portion.

2. The system of claim 1 further comprising a removal tool for removing the specimen from said specimen chamber, said removal tool comprising a handle portion integrally formed with a mating tip, at least a portion of said mating tip being threaded.

3. The system of claim 1, wherein said mating portion of said applicator further comprises:

a hollow casing including a first end portion, a second end portion, and a cavity that extends between said end portions and is defined by oppositely disposed first and second surfaces, said first end portion including at least two retractable pins for mating with a plurality of openings in said plunger, said second end portion being integrally formed with said main body portion of said applicator; and an actuator member disposed within said casing and being operably linked to said handle portion;

wherein each of said retractable pins extends transversely to, and is in contact with, said actuator member.

4. The system of claim 1 further comprising a disc-shaped specimen holder for placement into said specimen chamber, said specimen holder comprising a plurality of pores extending between oppositely disposed first and second surfaces and a threaded mating aperture that also extends between said first and second surfaces.

5. A method for vitrifying a biological specimen, said method comprising the steps of:

providing a system comprising an apparatus and an applicator;

said apparatus comprising:

a cap member including a stem portion integrally formed with a receiving portion, said receiving portion having a disc-like shape and including an outer surface, said outer surface including a first skirt member comprised of a heat-sealable material, said first skirt member being attached along a circumferential portion of said outer surface;

a tubular plunger having an open first end portion and a closed second end portion; and a specimen chamber for receiving said plunger, said specimen chamber having an open first end portion, a closed second end portion, and a cavity extending between said first and second end portions, said cavity being defined by oppositely disposed inner and outer surfaces, said specimen chamber further including a second skirt member comprised of heat-sealable material, said second skirt member being attached along a circumferential portion of said outer surface; and said applicator comprising a mating portion, a handle portion, and a main body portion extending between said mating portion and said handle portion;

said mating portion comprising a hollow casing and an actuator member, said casing including a first end portion, a second end portion, and a cavity that extends between said end portions and is defined by oppositely disposed first and second surfaces, said first end portion including at least two retractable pins for mating with said plurality of openings of said plunger, said second end portion being integrally formed with said main body portion of said applicator, said actuator member being disposed within said casing and operably linked to said handle portion, wherein each of said retractable pins extend transversely to, and are in contact with, said actuator member;

placing said biological specimen in the specimen chamber;

adding a first vitrification solution into said specimen chamber;

inserting said plunger into the specimen chamber;

mating said receiving portion of the said cap member with said first end portion of said specimen chamber; and applying a cooling fluid to said apparatus to vitrify said biological specimen.

6. The method of claim 5, wherein said step of placing the specimen in the specimen chamber further comprises the steps of:

placing the disc-shaped specimen platform into the specimen chamber after adding a vitrification solution into the specimen chamber, the specimen platform comprising a plurality of pores extending between oppositely disposed first and second surfaces and a threaded mating aperture also extending between the first and second surfaces.

7. The method of claim 6 further comprising the step of:

adding a second vitrification solution into the specimen chamber, the second vitrification solution having a cryoprotectant concentration greater than the cryoprotectant concentration in the first vitrification solution.

8. The method of claim 5, wherein said step of mating said receiving portion of said cap member with said first end portion of said specimen chamber further comprises the step of applying heat to said first and second skirt members so that a seal is formed between said first and second skirt members.

9. The method of claim 5, wherein said step of inserting the plunger into the specimen chamber further comprises the steps of:

manipulating said handle portion so that said pins are retracted into said casing;

mating said first end portion of said plunger with said first end portion of said casing; and manipulating said handle portion of said applicator so that each of said pins is respectively mated with each of said openings of said plunger.

10. The method of claim 8 further comprising the steps of:

removing said cap member from said specimen chamber;

removing said plunger from said specimen chamber;

providing a removal tool, said removal tool comprising a handle portion integrally formed with a mating tip, wherein at least a portion of said mating tip is threaded;

screwing said mating tip of said removal tool into said threaded mating aperture of said specimen platform; and withdrawing said removal tool from said specimen chamber.

11. The method of claim 5, wherein said biological specimen comprises viable single cells.

12. A method for vitrifying a biological specimen, said method comprising the steps of:

providing a system comprising an apparatus and an applicator, said apparatus comprising:

a cap member including a stem portion integrally formed with a receiving portion, said receiving portion having a disc-like shape and including an outer surface, said outer surface including a first skirt member comprised of a heat-sealable material, said first skirt member attached to said outer surface;

a tubular plunger having an open first end portion and a closed second end portion, said plunger comprising a channel that extends between said first and second end portions and is defined by inner and outer surfaces, said first end portion of the plunger including a plurality of openings extending between said inner and outer surfaces, said second end portion of the plunger including a ridge that extends circumferentially about said outer surface and a filtering member extending substantially perpendicular to said channel; and a specimen chamber for receiving said plunger, said specimen chamber having an open first end portion, a closed second end portion, and a cavity extending between said first and second end portions, said cavity being defined by oppositely disposed inner and outer surfaces, said specimen chamber further including a second skirt member comprised of heat-sealable material, said second skirt member being attached to said outer surface; and said applicator comprising a mating portion, a handle portion, and a main body portion extending between said mating portion and said handle portion;

said mating portion comprising a hollow casing and an actuator member, said casing including a first end portion, a second end portion, and a cavity that extends between said end portions and is defined by oppositely disposed first and second surfaces, said first end portion including at least two retractable pins for mating with said plurality of openings of said plunger, said second end portion being integrally formed with said main body portion of said applicator, said actuator member being disposed within said casing and operably linked to said handle portion, wherein each of said retractable pins extend transversely to, and are in contact with, said actuator member;

placing said biological specimen in said specimen chamber;

inserting said plunger into said specimen chamber;

mating said first open end of said specimen chamber with said receiving portion of said cap member; and applying a cooling fluid to said apparatus to vitrify said biological specimen.

13. The method of claim 12, wherein said step of placing said biological specimen in said specimen chamber further comprises the steps of:

providing a sealing member applicator, said sealing member applicator having an elongated, cup-like configuration with a first end portion, a second end portion, and a main body portion intermediate the end portions;

securing said at least one sealing member about said first end portion of said sealing member applicator;

securing a disposable filter at a first end of said sealing member applicator;

positioning said sealing member applicator so that said disposable filter contacts said filtering member of said plunger; and manipulating said at least one sealing member so that a portion of said disposable filter is sandwiched between said at least one sealing member and said plunger.

14. The method of claim 12, wherein said step of mating said receiving portion of said cap member with said first end portion of said specimen chamber further comprises the step of applying heat to said first and second skirt members so that a seal is formed between said first and second skirt members.

15. The method of claim 12, wherein said step of inserting said plunger into said specimen chamber further comprises the steps of:

manipulating said handle portion so that said pins are retracted into said casing;

mating said first end portion of said plunger with said first end portion of said casing; and manipulating said handle portion of said applicator so that each of said pins is respectively mated with each of said openings of said plunger.

16. The method of claim 12, wherein said step of placing said biological specimen in said specimen chamber further comprises the steps of:

adding a vitrification solution to said specimen chamber;

equilibrating said biological specimen; and removing excess vitrification solution from said specimen chamber.

17. The method of claim 12, wherein said biological specimen comprises viable tissues.

* * * * *